US012667288B1

(12) United States Patent
    Burke

(10) Patent No.: US 12,667,288 B1
(45) Date of Patent: Jun. 30, 2026

(54) SYSTEM AND METHOD FOR COMPUTERIZED STIMULUS PRESENTATION AND BEHAVIORAL INTERACTION MEASUREMENT

(71) Applicant: William Burke, Summerville, SC (US)

(72) Inventor: William Burke, Summerville, SC (US)

( * ) Notice: Subject to any disclaimer, the term of this patent is extended or adjusted under 35 U.S.C. 154(b) by 0 days.

(21) Appl. No.: 19/542,552

(22) Filed: Feb. 17, 2026

(51) Int. Cl.
    *A61B 5/16* (2006.01)
    *A61B 5/00* (2006.01)
    *G16H 50/30* (2018.01)

(52) U.S. Cl.
    CPC .............. *A61B 5/162* (2013.01); *A61B 5/742* (2013.01); *G16H 50/30* (2018.01)

(58) Field of Classification Search
    None
    See application file for complete search history.

(56) References Cited

U.S. PATENT DOCUMENTS

2022/0133195 A1* 5/2022 Iacoviello .............. G16H 50/30

* cited by examiner

*Primary Examiner* — Matthew Kremer
(74) *Attorney, Agent, or Firm* — Gregory Finch; Finch Paolino, LLC

(57) ABSTRACT

A computerized behavioral measurement system, method, and computer-readable medium are disclosed. The system includes a display, one or more input devices, at least one processor, and memory storing instructions that cause the system to present a sequence of visual stimuli comprising photographs of human subjects. For each stimulus, the system enforces at least one of a presentation interval and a response window, receives a participant response during the response window, and measures an interaction metric comprising a dwell-time metric for the stimulus and/or a defined region-of-interest. The system generates and stores a machine-readable output record comprising category-segmented response metrics and may normalize such metrics to produce participant-specific normalized metrics. In certain embodiments, a second task module presents lexical stimuli and generates a unified output record including visual-task metrics and lexical error rate.

20 Claims, 19 Drawing Sheets

1200a

In this portion of the test you will view pictures of adult and adolescent males.

You will be asked to choose the level of threat they may pose.
(1) No Threat
(2) Possible Threat
(3) Dangerous Threat Start Press the corresponding number or click the corresponding button, then press the
ENTER key to advance to the next item There is a 10 second time limit per slide 1200b (1) No Threat (2) Possible Threat (3) Dangerous Threat Enter 1200d In this portion of the test you will view text.

You will be asked to decide if the text is a word or non word.
(1) Yes
(2) No

Press the corresponding number or click the corresponding button, then press the
ENTER key to advance to the next item There is a 2 second time limit per slide Start

SYSTEM AND METHOD FOR COMPUTERIZED STIMULUS PRESENTATION AND BEHAVIORAL INTERACTION MEASUREMENT

FIELD

The present disclosure relates to the field of computerized behavioral assessment and measurement systems; in particular, systems and methods for presenting timed stimuli, capturing non-volitional user interaction metrics, and generating participant-specific response outputs.

BACKGROUND

Assessing human perception and decision-making in high-stakes environments presents persistent challenges for agencies and organizations responsible for training, screening, and professional development. In many contexts, evaluators seek tools that can measure how individuals process and react to visual information presented under controlled conditions, including time-pressured scenarios that may implicate safety, judgment, and situational awareness.

Conventional assessment approaches often rely on self-report questionnaires, interviews, or observer-based evaluations. While these techniques can be useful, they may be susceptible to response bias, coaching effects, inconsistent administration, and limited repeatability. In addition, assessments that depend heavily on subjective interpretation may exhibit variability across evaluators, settings, and populations, which can complicate efforts to compare results within an individual over time or across different test sessions.

Computer-based assessments have been introduced to improve standardization and scalability. However, many existing computerized approaches primarily capture explicit responses (e.g., selected answers) and may not reliably capture other behavioral indicators, such as attention-related interaction patterns, under uniform timing and presentation constraints. Further, some approaches can be influenced by participant awareness of what is being measured, potentially affecting test behavior and undermining the fidelity of results.

Accordingly, there remains a need for improved assessment frameworks that can be administered in a consistent, repeatable manner, that can reduce variability introduced by human administration and scoring, and that can provide robust measurement of participant performance under controlled presentation conditions. Through applied effort, ingenuity, and innovation, Applicant has identified a number of deficiencies and problems with existing computerized behavioral assessments and related testing methodologies. Applicant has developed a solution that is embodied by the present invention, which is described in detail below.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present disclosure relates generally to computerized behavioral measurement and testing systems and, more particularly, to systems, methods, and computer-readable media for presenting visual and lexical stimuli under controlled conditions, capturing participant interaction metrics and responses, and generating machine-readable output records representative of participant performance.

In one aspect, the present disclosure provides a computerized behavioral measurement system that includes a display, one or more input devices, at least one processor, and memory storing instructions that, when executed, cause the system to present, via the display, a sequence of visual stimuli each associated with a stimulus identifier and a stimulus category. In some embodiments, the sequence of visual stimuli includes a sequence of photographs of human subjects, wherein the stimulus identifier comprises race or ethnicity of the human subject, and wherein the stimulus category comprises a level of threat associated with the human subject. The system is further configured to enforce, for each visual stimulus, at least one of a presentation interval and a response window; to receive, via the one or more input devices and during the response window, a participant response associated with the stimulus identifier; and to measure, during presentation of the visual stimulus, an interaction metric comprising a dwell-time metric associated with at least one of the visual stimulus or a region-of-interest of the visual stimulus. The system is further configured to generate, from the participant responses and the interaction metric, a machine-readable output record comprising category-segmented response metrics for the participant, and to store the machine-readable output record in a non-transitory storage medium.

In certain embodiments, measuring the dwell-time metric includes measuring, without expressly prompting the participant to provide the dwell-time metric, an elapsed time corresponding to participant attention to the visual stimulus based on event data captured by the system. The event data may include, by way of example, cursor-position events, pointer-movement events, click events, keystroke events, scrolling events, viewport-focus events, window-focus events, or touch-input events. In some embodiments, the region-of-interest is defined by region metadata stored in association with the stimulus identifier, and measuring the dwell-time metric includes accumulating elapsed time while the event data indicates a participant focus within the region-of-interest.

In certain embodiments, enforcing the presentation interval and/or the response window includes disabling one or more of stimulus skipping, stimulus replay, stimulus backtracking, or response submission outside the response window. In certain embodiments, presenting the sequence of visual stimuli includes selecting the sequence according to a session policy that enforces one or more of randomized ordering, counterbalanced ordering across stimulus categories, or a minimum quantity of stimuli per stimulus category. In certain embodiments, the category-segmented response metrics include one or more of per-category accuracy, per-category error rate, per-category response-distribution statistics, per-category dwell-time statistics, or per-category response-time statistics.

In another aspect, the present disclosure provides a computer-implemented method that includes presenting, on a display, a sequence of visual stimuli each associated with a stimulus identifier and a stimulus category. In some embodiments, the sequence of visual stimuli includes a sequence of photographs of human subjects, wherein the stimulus identifier comprises race or ethnicity of the human subject, and wherein the stimulus category comprises a level of threat associated with the human subject. For each presented visual stimulus, the method includes enforcing at least one of a presentation interval and a response window; capturing a participant response associated with the stimulus identifier during the response window; and measuring, during presentation of the visual stimulus, an interaction metric comprising a dwell-time metric associated with at least one of the visual stimulus or a region-of-interest of the visual stimulus. The method further includes generating, based on the participant responses and the interaction metric, category-segmented response metrics for the participant; normalizing the category-segmented response metrics to produce participant-specific normalized metrics by comparing at least a first category-segmented response metric to at least a second category-segmented response metric for the same participant; and outputting and storing a machine-readable output record comprising the participant-specific normalized metrics.

In certain embodiments of the method, normalizing includes generating an ipsative metric by computing, for the participant, a deviation of a category-segmented response metric from an aggregate metric across multiple stimulus categories for the participant. In certain embodiments, normalizing includes scaling at least one category-segmented response metric using one or more of z-score normalization, min-max scaling, rank-order normalization, or vector normalization computed over metrics of the same participant. In certain embodiments, measuring the dwell-time metric includes computing the dwell-time metric from event data captured by the system without expressly requesting the dwell-time metric from the participant. In certain embodiments, generating the category-segmented response metrics includes generating one or more of an under-classification rate, an over-classification rate, or a confusion matrix based on participant responses mapped to a set of allowed response classes. In certain embodiments, enforcing includes disabling one or more of stimulus backtracking, stimulus replay, or response entry outside the response window. In certain embodiments, the method further includes storing, in association with the machine-readable output record, session metadata including one or more of device identifiers, display parameters, timing parameters, stimulus identifiers presented, or an ordering of the presented stimuli.

In another aspect, the present disclosure provides a computerized behavioral testing system that includes a display, one or more input devices, at least one processor, and memory storing instructions that, when executed, cause the system to execute a first task module that presents scenario-based visual stimuli and captures participant classification responses under enforced response windows. In some embodiments, the scenario-based visual stimuli comprise photographs of human subjects including predetermined characteristics comprising race or ethnicity and facial expression. The system is further configured to execute a second task module that presents lexical stimuli comprising letter strings and captures participant lexical-decision responses indicating whether each letter string is a word or a non-word under enforced response windows; to compute, for the first task module, at least one category-segmented visual-task metric; to compute, for the second task module, at least one lexical-task metric comprising a lexical error rate; and to generate and store a unified machine-readable output record comprising the category-segmented visual-task metric and the lexical-task metric for the participant.

In certain embodiments, the first task module further measures an interaction metric comprising a dwell-time metric associated with at least one visual stimulus or a region-of-interest of the visual stimulus. In certain embodiments, the lexical stimuli comprise at least two lexical stimulus sets selected from a static word set, an emotive word set, and a nonsense letter-string set, and the lexical-task metric comprises separate accuracy values for each lexical stimulus set. In certain embodiments, the system further comprises a session orchestrator configured to interleave the first task module and the second task module according to a session policy that enforces one or more of randomized ordering, counterbalanced ordering, or minimum counts per task module. In certain embodiments, generating the unified machine-readable output record comprises generating a participant-specific output vector comprising at least the category-segmented visual-task metric, the lexical error rate, and at least one timing-derived metric. In certain embodiments, the system is configured to export the unified machine-readable output record in a structured format comprising JSON, XML, or a tabular file format for downstream processing by an external computing system.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The systems and methods of the present disclosure may be better understood from the following illustrative description with reference to the following drawings in which.

DETAILED DESCRIPTION

Figure 1:
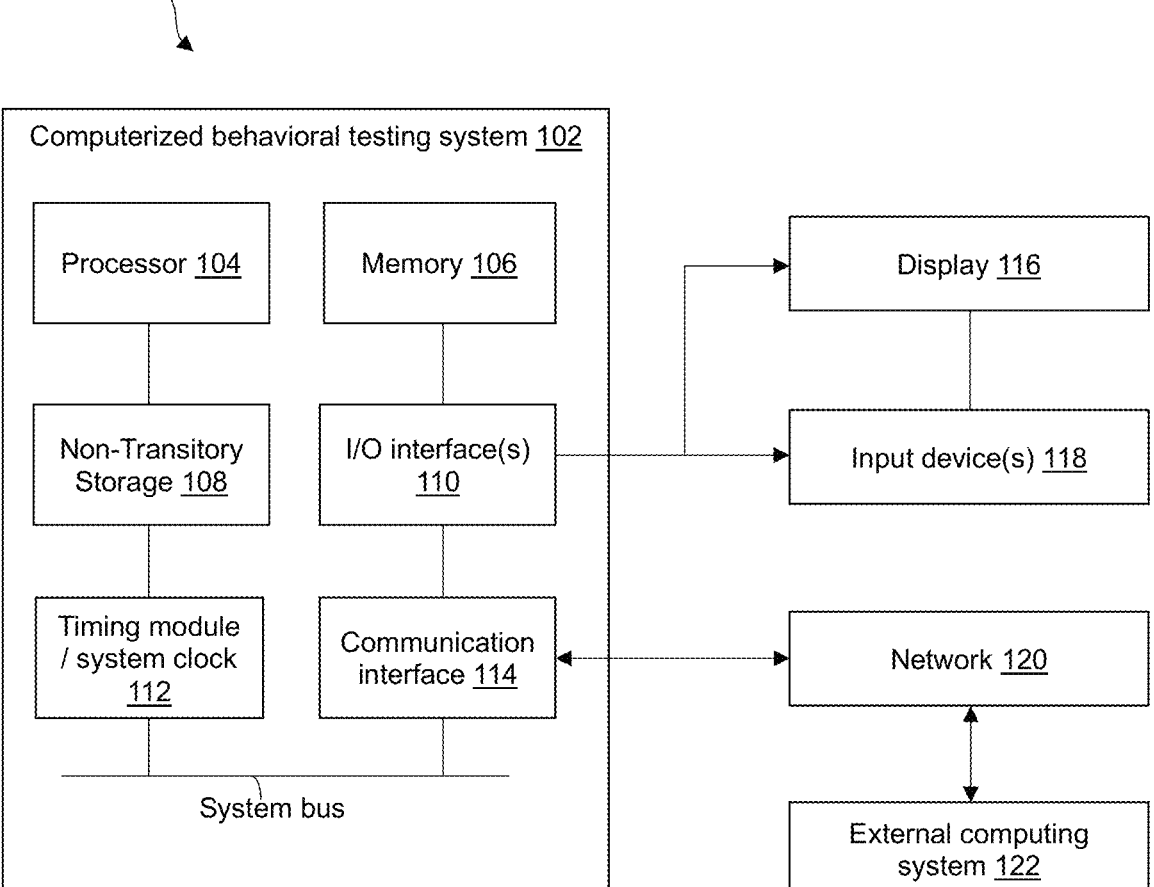
FIG. 1 is a block diagram illustrating a computerized behavioral measurement and testing system, according to certain aspects of the present disclosure.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems configured to present visual and lexical stimuli to a participant under controlled timing and sequencing constraints, to capture participant responses and associated interaction metrics during enforced response windows, to compute and store category-segmented and participant-specific normalized performance metrics based at least in part on the captured responses and interaction metrics, and to generate and output machine-readable records representative of participant performance. The various concepts and embodiments described herein may be implemented in hardware, software, firmware, or any combination thereof, and may be practiced with one or more processors, computing devices, displays, input devices, and associated storage.

In certain embodiments, the disclosed system measures participant attention or focus without requiring an express prompt requesting attention data and without requiring specialized sensing hardware. For example, the system may compute a dwell-time metric from time-stamped interaction event data captured during stimulus presentation, such as cursor-position events, pointer-movement events, click events, scrolling events, viewport-focus events, window-focus events, and/or touch-input events. In these embodiments, the dwell-time metric is derived from the participant's interaction behavior as the participant completes the task, thereby providing an attention-related measurement channel that is distinct from, and complementary to, the participant's explicit classification response.

In certain embodiments, the system conditions dwell-time computation on one or more validity gates so that computed dwell time corresponds to periods in which the stimulus is actually viewable and within defined timing boundaries. For example, event data may be filtered to exclude events occurring outside a stimulus presentation interval and/or response window boundaries, and may further be filtered based on application focus and viewport visibility (e.g., excluding periods in which a test window is not in focus or the stimulus is not visible). In this manner, the dwell-time metric can reflect controlled, session-consistent viewing intervals suitable for category-based aggregation and downstream analysis.

In certain embodiments, the system generates participant-specific normalized metrics that enable within-participant comparisons across stimulus categories and reduce reliance on population-level baselines. For example, category-segmented response metrics (e.g., per-category accuracy, error rate, dwell-time statistics, and/or response-time statistics) may be normalized by comparing at least one category metric to another category metric for the same participant and/or to an aggregate metric computed across categories for that participant. Such participant-specific normalization may include ipsative metrics representing deviations from the participant's own aggregate performance, thereby yielding individualized outputs that remain interpretable across sessions and that support longitudinal monitoring of category-dependent patterns.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Before the present invention and specific exemplary embodiments of the invention are described, it is to be understood that this invention is not limited to the particular embodiments described, and as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, "exemplary" means serving as an example or illustration and does not necessarily denote ideal or best.

As used herein, the term "includes" means includes but is not limited to, the term "including" means including but not limited to. The term "based on" means based at least in part on.

As used herein, the term "interface" refers to any shared boundary across which two or more separate components of a computer system may exchange information. The exchange can be between software, computer hardware, peripheral devices, humans, and combinations thereof.

As used herein, the term "computerized" means implemented at least in part by one or more computing devices including at least one processor and memory executing stored instructions.

As used herein, the term "system" means one or more components, modules, or devices operatively coupled to perform one or more functions, and may be implemented as a single device or distributed across multiple devices.

As used herein, the term "computerized behavioral measurement system" means a computerized system configured to present one or more stimuli to a participant, capture participant input and/or interaction metrics associated with presentation of the stimuli, and generate one or more output records based on the captured data.

As used herein, the term "computerized behavioral testing system" means a computerized behavioral measurement system configured to execute at least two distinct task modules during a testing session and generate a unified output record derived from the task modules.

As used herein, the term "display" means any device or component configured to present visual information to a participant, including a monitor, touchscreen, head-mounted display, projector, or other visual output device.

As used herein, the term "input device" means any device configured to receive participant input or interaction data, including a keyboard, mouse, trackpad, touchscreen, controller, microphone, camera, sensor, or other device capable of capturing participant actions or events.

As used herein, the term "processor" means one or more processing elements, cores, or circuits configured to execute instructions, including a CPU, GPU, microcontroller, DSP, FPGA, ASIC, or combinations thereof.

As used herein, the term "memory" means one or more non-transitory computer-readable storage media configured to store data and/or instructions, including RAM, ROM, flash memory, magnetic storage, optical storage, or combinations thereof.

As used herein, the term "instructions" means computer-executable code, logic, firmware, and/or configuration data that, when executed by one or more processors, causes performance of one or more operations.

As used herein, the term "present" means render, output, or otherwise display stimuli on a display for perception by a participant.

As used herein, the term "sequence" means an ordered set of two or more items, which may be fixed, randomized, pseudo-randomized, counterbalanced, adaptive, or otherwise determined according to a policy.

As used herein, the term "visual stimulus" means any visual content presented to a participant, including an image, photograph, graphic, video frame, scene depiction, or other visual depiction.

As used herein, the term "scenario-based visual stimulus" means a visual stimulus depicting a scene or context intended to elicit a participant classification response, including depictions of persons in different settings and/or situations.

As used herein, the term "photograph" means an image representing a captured or rendered depiction of one or more subjects, whether obtained by camera capture, synthesis, or other image generation or storage technique.

As used herein, the term "human subject" means a depicted person in a visual stimulus.

As used herein, the term "predetermined characteristics" means one or more attributes assigned, tagged, curated, or otherwise associated with a stimulus prior to presentation, including demographic or non-demographic attributes.

As used herein, the term "race or ethnicity" means an identifier representing a demographic category attributed to a depicted human subject for purposes of stimulus tagging or categorization.

As used herein, the term "stimulus identifier" means data that identifies a stimulus and/or one or more attributes associated with the stimulus, including an alphanumeric identifier, metadata, and/or one or more characteristic tags.

As used herein, the term "stimulus category" means data representing a classification, grouping, or label assigned to a stimulus for analysis or segmentation, including one or more task-relevant categories.

As used herein, the term "level of threat" means a stimulus category label indicating a threat-class classification associated with a stimulus for purposes of participant response capture and metric generation, without requiring any clinical or psychological diagnosis.

As used herein, the term "presentation interval" means a time duration for which a stimulus is presented and/or for which presentation is controlled by the system.

As used herein, the term "response window" means a time interval during which participant responses are accepted, recorded, and/or considered valid by the system.

As used herein, the term "enforce" means to control system operation to apply one or more constraints, including timing constraints and/or interaction constraints, such as disabling, preventing, limiting, or rejecting actions that violate the constraints.

As used herein, the term "participant response" means any participant-provided input associated with a presented stimulus, including a classification selection, rating, decision input, or other input captured via one or more input devices.

As used herein, the term "classification response" means a participant response selecting among multiple allowed response classes for a stimulus.

As used herein, the term "interaction metric" means a quantitative measure derived at least in part from participant interaction with the system during stimulus presentation, including timing, event-derived, or attention-pro14 measures.

As used herein, the term "dwell-time metric" means a quantitative measure of elapsed time associated with a participant's interaction with, attention to, or focus on a stimulus or region-of-interest during a defined interval, including time computed from event data and/or system state.

As used herein, the term "region-of-interest" means a defined portion of a visual stimulus or display area for which interaction metrics are separately measured or computed.

As used herein, the term "region metadata" means data defining and/or describing a region-of-interest, including coordinates, boundaries, masks, bounding boxes, or other parameters usable to identify the region-of-interest.

As used herein, the term "event data" means one or more recorded events reflecting participant interaction and/or system state, including cursor-position events, pointer-movement events, click events, keystroke events, scrolling events, viewport-focus events, window-focus events, touch-input events, and/or other interaction events.

As used herein, the term "machine-readable" means structured such that it is parseable, processable, or interpretable by a computing system, including through a defined schema or data structure.

As used herein, the term "output record" means a data structure or stored set of data generated by the system representing results, metrics, and/or session information for a participant and/or session.

As used herein, the term "machine-readable output record" means an output record stored in a structured format suitable for electronic processing by a computing system.

As used herein, the term "category-segmented" means separated, grouped, or partitioned according to stimulus categories and/or other defined category labels.

As used herein, the term "category-segmented response metrics" means one or more computed metrics derived from participant responses and/or interaction metrics, partitioned by stimulus category, including accuracy, error rate, response distributions, dwell-time statistics, response-time statistics, or combinations thereof.

As used herein, the term "visual-task metric" means a metric computed from participant responses and/or interaction metrics associated with a visual stimulus task.

As used herein, the term "lexical stimulus" means a presented stimulus comprising one or more letter strings.

As used herein, the term "letter string" means a sequence of characters presented as a candidate word or non-word.

As used herein, the term "lexical-decision response" means a participant response indicating whether a presented letter string is classified as a word or a non-word.

As used herein, the term "lexical-task metric" means a metric computed from responses to lexical stimuli, including accuracy, error rate, and/or response time measures.

As used herein, the term "lexical error rate" means a proportion, rate, count, or other measure representing incorrect lexical-decision responses for a defined set of lexical stimuli.

As used herein, the term "static word set" means a set of lexical stimuli designated as neutral or non-emotive words for testing purposes.

As used herein, the term "emotive word set" means a set of lexical stimuli designated as emotionally laden words for testing purposes.

As used herein, the term "nonsense letter-string set" means a set of lexical stimuli designated as non-words for testing purposes.

As used herein, the term "task module" means software, firmware, and/or logic configured to perform a defined testing task, including presenting stimuli, capturing responses, and computing one or more metrics associated with the task.

As used herein, the term "first task module" means a task module configured to present scenario-based visual stimuli and capture participant classification responses under enforced response windows.

As used herein, the term "second task module" means a task module configured to present lexical stimuli and capture participant lexical-decision responses under enforced response windows.

As used herein, the term "session orchestrator" means software, firmware, and/or logic configured to control execution, ordering, and/or interleaving of tasks and stimuli during a session according to one or more session policies.

As used herein, the term "interleave" means to alternate, mix, or sequence operations of two or more task modules within a session in accordance with a policy.

As used herein, the term "session policy" means one or more rules, parameters, and/or constraints used to control sequencing of stimuli and/or tasks, including randomized ordering, counterbalanced ordering, minimum counts, and/or other ordering constraints.

As used herein, the term "randomized ordering" means an ordering determined at least in part by a random or pseudo-random process.

As used herein, the term "counterbalanced ordering" means an ordering selected to balance presentation across categories and/or conditions, including balancing the frequency or ordering of categories across a session or across participants.

As used herein, the term "normalize" means to compute one or more transformed metrics from one or more underlying metrics to place the metrics on a comparable scale or representation, including by scaling, centering, ranking, or other transformation.

As used herein, the term "participant-specific normalized metrics" means normalized metrics computed for a participant based on comparisons among metrics of that same participant, including comparisons across stimulus categories.

As used herein, the term "ipsative metric" means a participant-specific normalized metric computed by comparing the participant's performance across different categories or conditions relative to the participant's own aggregate or baseline values.

As used herein, the term "aggregate metric" means a metric computed by combining or summarizing metrics across multiple categories or conditions, including by average, median, weighted combination, or other aggregation.

As used herein, the term "deviation" means a difference, residual, distance, or other measure representing variation of a metric from a reference value.

As used herein, the term "z-score normalization" means a normalization in which a metric is transformed using a mean and standard deviation.

As used herein, the term "min-max scaling" means a normalization in which a metric is scaled relative to a minimum and maximum.

As used herein, the term "rank-order normalization" means a normalization in which a metric is transformed based on rank ordering.

As used herein, the term "vector normalization" means a normalization in which a set of metrics is scaled based on a vector magnitude or other vector norm.

As used herein, the term "under-classification rate" means a metric representing frequency or rate of assigning a lower class than a reference class among allowed response classes.

As used herein, the term "over-classification rate" means a metric representing frequency or rate of assigning a higher class than a reference class among allowed response classes.

As used herein, the term "confusion matrix" means a data structure representing counts, rates, or proportions of predicted or selected classes versus reference classes across allowed response classes.

As used herein, the term "allowed response classes" means a predefined set of selectable response categories for a classification response.

As used herein, the term "session metadata" means data associated with a session that describes one or more aspects of administration or execution of the session, including device identifiers, display parameters, timing parameters, presented stimuli identifiers, and/or ordering of presented stimuli.

As used herein, the term "device identifier" means data identifying a device used to execute or administer a session, including a hardware identifier, network identifier, assigned identifier, or other identifier.

As used herein, the term "display parameters" means data describing display configuration and/or operation, including resolution, scaling, refresh rate, brightness, and/or other display settings.

As used herein, the term "timing parameters" means data specifying timing constraints or values, including presentation intervals, response windows, delays, and/or timestamps.

As used herein, the term "unified machine-readable output record" means a machine-readable output record that includes results and/or metrics generated from two or more task modules.

As used herein, the term "participant-specific output vector" means a structured set of values representing participant metrics, including one or more visual-task metrics, one or more lexical-task metrics, and optionally one or more timing-derived metrics.

As used herein, the term "timing-derived metric" means a metric computed at least in part from timing information, including response times, dwell times, latencies, or statistics derived therefrom.

As used herein, the term "non-transitory storage medium" means one or more non-transitory computer-readable storage media that store data and/or instructions, excluding transitory propagating signals.

As used herein, the term "export" means outputting or transmitting data from the system in a defined format for storage and/or use by another system or component.

As used herein, the term "structured format" means a format organized according to a schema or defined structure, including JSON, XML, and tabular formats.

As used herein, the term "tabular file format" means a structured format arranged in rows and columns, including CSV or similar tabular representations.

As used herein, the term "external computing system" means a computing system separate from the system performing the testing session and configured to receive, parse, store, or further process the exported output record.

The present disclosure generally relates to computerized systems and methods for administering structured behavioral assessments using controlled stimulus presentation. In various embodiments, a computing system presents visual stimuli to a participant under defined timing and sequencing constraints, captures participant responses within enforced response windows, and measures interaction metrics generated during stimulus presentation. The system processes the captured responses and interaction metrics to compute participant performance measures and to generate machine-readable output records suitable for storage, reporting, and downstream analysis.

In certain embodiments, the visual assessment component presents scenario-based images that are tagged or otherwise associated with stimulus identifiers and stimulus categories. The system computes category-segmented response metrics, such as accuracy measures, error rates, response distributions, and timing-related statistics, and may further normalize such metrics on a participant-specific basis to produce normalized outputs derived from comparisons within the same participant. The resulting output record can provide a structured representation of participant performance across stimulus categories under controlled administration conditions.

In certain embodiments, the system further includes multiple task modules within a single session, such as a visual stimulus task and a lexical decision task using letter-string stimuli. The system may compute respective metrics for each task module and generate a unified output record combining the visual-task metrics with lexical-task metrics, thereby providing an integrated, machine-readable assessment record generated from multiple controlled stimulus-response tasks.

Certain benefits and advantages of the present disclosure include improved standardization of behavioral testing through computerized presentation of stimuli under controlled timing and sequencing constraints.

Certain benefits and advantages of the present disclosure include enforcing response windows and other interaction constraints to reduce variability introduced by inconsistent administration and to improve repeatability across sessions.

Certain benefits and advantages of the present disclosure include capturing participant responses and interaction metrics in a uniform, machine-readable manner suitable for storage, auditing, and downstream processing.

Certain benefits and advantages of the present disclosure include measuring interaction metrics, including dwell-time metrics associated with presented stimuli and/or defined regions-of-interest, to provide additional quantitative signals beyond explicit participant selections.

Certain benefits and advantages of the present disclosure include generating category-segmented response metrics that facilitate analysis of performance across stimulus categories while maintaining a consistent computational framework.

Certain benefits and advantages of the present disclosure include generating participant-specific normalized metrics (including ipsative metrics) that support within-participant comparisons across categories and over time.

Certain benefits and advantages of the present disclosure include supporting multi-module assessments, including combinations of visual scenario tasks and lexical decision tasks, to produce a unified output record that consolidates metrics from multiple task types.

Certain benefits and advantages of the present disclosure include exporting structured output records in standardized formats to facilitate interoperability with external systems for reporting, training support, compliance workflows, and analytics.

Turning now descriptively to the drawings, in which similar reference characters denote similar elements throughout the several views, FIG. 1 depicts a block diagram illustrating an example computerized behavioral testing system 102 suitable for implementing the systems and methods described herein. In the illustrated embodiment, the computerized behavioral testing system 102 includes one or more processors 104 operatively coupled to memory 106 and non-transitory storage 108 via a system bus 100. The processor(s) 104 may include one or more general-purpose processors, microcontrollers, digital signal processors, graphics processing units, application-specific integrated circuits, field-programmable gate arrays, or combinations thereof, and may be configured to execute computer-executable instructions stored in memory 106 and/or non-transitory storage 108. Memory 106 may include volatile and/or non-volatile memory used to store instructions and data during operation, and non-transitory storage 108 may include one or more non-transitory computer-readable storage media configured to store persistent data, including, by way of example, stimulus libraries, stimulus metadata, region metadata, session parameters, participant responses, interaction event data, computed metrics, and machine-readable output records.

The computerized behavioral testing system 102 further includes one or more input/output (I/O) interfaces 110 configured to provide communication between the system bus 100 and one or more peripheral devices. In the illustrated embodiment, a display 116 is coupled to the I/O interface(s) 110 and is configured to present visual information to a participant, including visual stimuli and/or lexical stimuli. One or more input device(s) 118 are also coupled to the I/O interface(s) 110 and are configured to receive participant inputs and/or interaction event data, including, by way of example, keyboard input, mouse or pointer input, touch input, controller input, and other user interaction signals. In certain embodiments, the display 116 and input device(s) 118 may be integrated (e.g., a touchscreen device) and/or may be provided by a client device operatively coupled to the computerized behavioral testing system 102.

In the illustrated embodiment, the computerized behavioral testing system 102 further includes a timing module and/or system clock 112, which may be configured to provide timing signals used to control one or more timing constraints during operation, including, for example, presentation intervals, response windows, timestamping of interaction events, and measurement of timing-derived metrics. The timing module/system clock 112 may be implemented in hardware, software, firmware, or combinations thereof.

The computerized behavioral testing system 102 may further include a communication interface 114 configured to communicate with one or more external systems via a network 120. The communication interface 114 may include wired and/or wireless interfaces and may implement one or more communication protocols. As shown, the system 102 may communicate, via the network 120, with an external computing system 122. In certain embodiments, the external computing system 122 may be configured to receive machine-readable output records generated by the computerized behavioral testing system 102 for storage, reporting, analytics, training support, or other downstream processing. The network 120 may include any suitable network or combination of networks, including a local area network, wide area network, the Internet, or combinations thereof.

Although FIG. 1 depicts a particular arrangement of components, it will be appreciated that the illustrated components are provided by way of example and may be combined, divided, replicated, omitted, or implemented in other suitable arrangements. For example, in some embodiments, the computerized behavioral testing system 102 may be implemented as a single computing device, while in other embodiments, functions of the system 102 may be distributed across multiple computing devices that communicate via the network 120.

Figure 2:
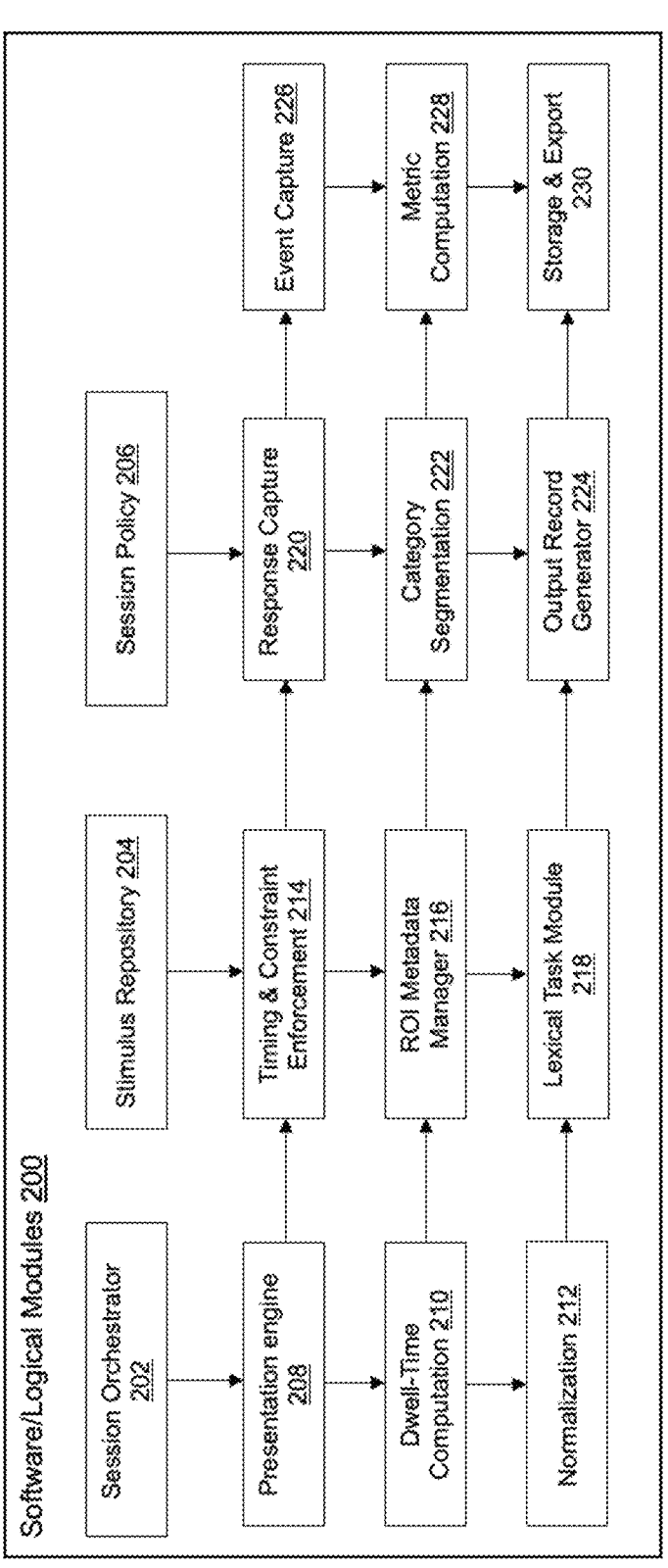
FIG. 2 is a block diagram illustrating exemplary software modules executable by the system of FIG. 1.

Referring now to FIG. 2, a block diagram illustrating example software and/or logical modules 200 is shown. In accordance with certain aspects of the present disclosure, software and/or logical modules 200 are executable by, or otherwise implemented in connection with, a computerized behavioral testing system (e.g., system 102 of FIG. 1). The modules 200 may be implemented in software, firmware, hardware, or any combination thereof, and may be executed by one or more processors to perform the functions described herein.

In the illustrated embodiment, a session orchestrator 202 controls overall administration of a testing session, including initiating, coordinating, and/or sequencing operations of one or more task modules and related processing modules. The session orchestrator 202 may access a stimulus repository 204, which stores or provides access to stimuli and associated metadata. In various embodiments, the stimulus repository 204 may include visual stimuli (e.g., images) and lexical stimuli (e.g., letter strings), along with associated stimulus identifiers and stimulus category tags usable for analysis and segmentation. The session orchestrator 202 may further access or apply a session policy 206 that specifies one or more rules and/or parameters for session execution, including, for example, ordering of stimuli, randomized ordering, counterbalanced ordering across stimulus categories, minimum numbers of stimuli per category and/or per task module, interleaving of task modules, and/or other session constraints.

A presentation engine 208 is configured to present stimuli to a participant, for example via a display. In certain embodiments, the presentation engine 208 retrieves stimuli and associated metadata from the stimulus repository 204 and presents the stimuli according to session parameters provided by the session orchestrator 202 and/or the session policy 206. A timing and constraint enforcement module 214 is configured to enforce one or more constraints during stimulus presentation and response capture, including, for example, enforcing presentation intervals, enforcing response windows, and/or disabling or preventing prohibited interactions such as stimulus skipping, backtracking, replay, or response submission outside of an authorized response window. In some embodiments, the timing and constraint enforcement module 214 provides timing boundaries and/or control signals to the presentation engine 208 and/or other modules to implement such constraints.

A response capture module 220 is configured to receive participant responses associated with presented stimuli, including, for example, classification responses, ratings, or other inputs. In some embodiments, the response capture module 220 time-stamps responses and associates captured responses with corresponding stimulus identifiers and/or stimulus categories. In the illustrated embodiment, an event capture module 226 is configured to capture interaction event data generated during participant interaction with the system, including, by way of example, cursor-position events, pointer-movement events, click events, keystroke events, scrolling events, viewport-focus events, window-focus events, touch events, and/or other interaction events. In certain embodiments, the event capture module 226 collects and time-stamps such event data for use in computing interaction metrics.

A dwell-time computation module 210 is configured to compute one or more dwell-time metrics associated with a presented stimulus and/or a region-of-interest of the stimulus. In some embodiments, the dwell-time computation module 210 computes dwell time based on event data captured by the event capture module 226 and timing information associated with stimulus presentation (e.g., stimulus start and end times and/or response-window boundaries), without expressly prompting the participant to provide dwell-time values. In the illustrated embodiment, an ROI metadata manager 216 is configured to store, retrieve, and/or manage region metadata defining one or more regions-of-interest associated with particular stimuli (e.g., via coordinates, bounding boxes, masks, or other region definition parameters). In certain embodiments, the dwell-time computation module 210 uses region metadata from the ROI metadata manager 216 to compute ROI-specific dwell-time metrics in addition to, or instead of, whole-stimulus dwell-time metrics.

A category segmentation module 222 is configured to segment captured data by stimulus category. For example, the category segmentation module 222 may group responses captured by the response capture module 220 and interaction metrics (e.g., dwell-time metrics) computed by the dwell-time computation module 210 into category-specific data-sets based on stimulus category tags. A metric computation module 228 is configured to compute one or more metrics from the segmented datasets, including, for example, category-segmented response metrics such as per-category accuracy, per-category error rates, per-category response distributions, per-category dwell-time statistics, and/or per-category response-time statistics. In certain embodiments, a normalization module 212 is configured to generate participant-specific normalized metrics (including ipsative metrics) by comparing at least one category-segmented response metric to at least another category-segmented response metric for the same participant and/or by comparing category-segmented metrics to an aggregate metric computed across multiple categories for the same participant.

In the illustrated embodiment, a lexical task module 218 is configured to administer a lexical task during a testing session, including presenting lexical stimuli (e.g., letter strings) and capturing lexical-decision responses indicating whether a presented letter string is a word or a non-word. The lexical task module 218 may compute one or more lexical-task metrics, including a lexical error rate, and provide such metrics for inclusion in a unified output record. In certain embodiments, the session orchestrator 202 coordinates execution of the lexical task module 218 with other session components, including interleaving lexical task trials with trials of a visual stimulus task administered via the presentation engine 208.

An output record generator 224 is configured to generate a machine-readable output record for a participant and/or session. In various embodiments, the output record generator 224 combines results and metrics computed by the metric computation module 228 and/or normalization module 212 and may further incorporate lexical-task metrics provided by the lexical task module 218. The output record generator 224 may additionally include session metadata, stimulus identifiers presented, ordering information, and/or timing parameters in the output record. A storage and export module 230 is configured to store the machine-readable output record in a non-transitory storage medium and/or to export the output record in a structured format (e.g., JSON, XML, or a tabular file format) for downstream processing by an external computing system.

It will be appreciated that the arrangement and separation of modules shown in FIG. 2 is provided by way of example. In various embodiments, certain modules may be combined, omitted, replicated, and/or implemented in alternative configurations, and data may flow between modules in different orders, without departing from the scope of the present disclosure.

Figure 3:
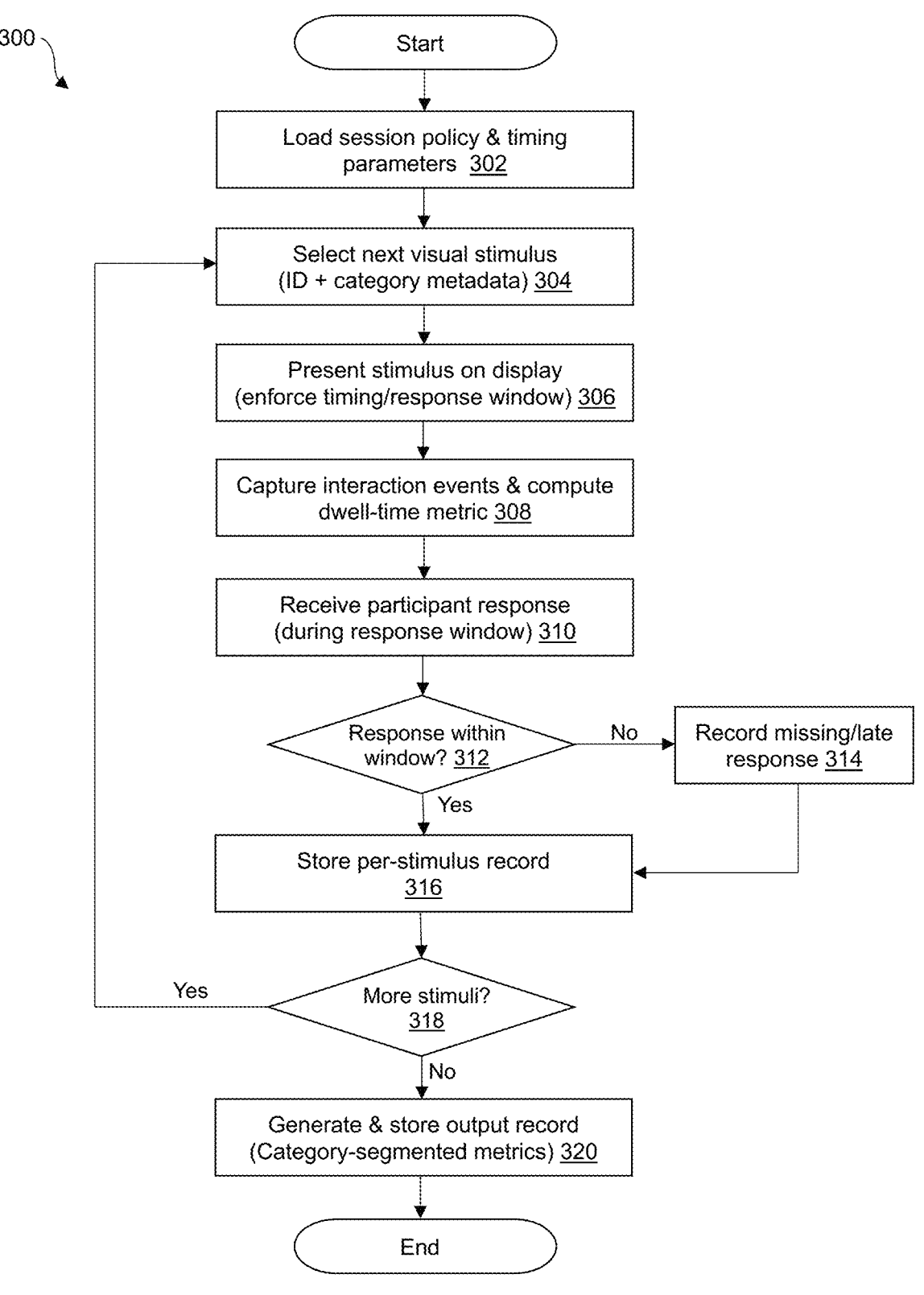
FIG. 3 is a flowchart illustrating an example method for administering a visual-stimulus task.

Referring now to FIG. 3, a flowchart illustrating an example method 300 for administering a visual-stimulus task using a computerized behavioral testing system (e.g., system 102 of FIG. 1) and associated software modules 200 (FIG. 2) is shown. In accordance with certain aspects of the present disclosure, method 300 may be performed by one or more processors executing instructions stored in memory, and may utilize one or more of the modules shown in FIG. 2, such as session orchestrator 202, stimulus repository 204, session policy 206, presentation engine 208, timing and constraint enforcement 214, response capture 220, event capture 226, dwell-time computation 210, output record generator 224, metric computation 228, and storage/export 230.

In accordance with certain aspects of the present disclosure, method 300 begins at Start and includes loading session policy and timing parameters at step 302. In various embodiments, the session policy and timing parameters define one or more administration constraints, including, by way of example, selection of a stimulus set for the session, randomized ordering and/or counterbalanced ordering of stimuli across one or more stimulus categories, minimum numbers of stimuli per stimulus category, presentation intervals, response window lengths, and/or constraints on participant navigation (e.g., disabling replay, backtracking, or skipping). At step 304, the system selects a next visual stimulus for presentation. In various embodiments, selecting the next visual stimulus includes retrieving, from the stimulus repository, the visual stimulus along with associated metadata comprising a stimulus identifier (ID) and one or more stimulus category tags. The stimulus ID may be used to associate participant responses and interaction metrics with the corresponding stimulus, and the stimulus category tags may be used to segment results for category-based analysis.

In accordance with certain aspects of the present disclosure, at step 306, the system presents the selected stimulus on a display and enforces one or more timing constraints, such as a presentation interval and/or a response window. In some embodiments, enforcing timing and response-window constraints includes controlling when a stimulus is displayed, controlling when response input is accepted, and/or implementing interface constraints such as disabling stimulus replay, disabling stimulus backtracking, disabling skipping to a subsequent stimulus before a presentation interval expires, and/or rejecting response submissions outside the response window. In certain embodiments, the system may time-stamp the stimulus presentation (e.g., stimulus onset and offset) for later computation of timing-derived metrics.

In accordance with certain aspects of the present disclosure, at step 308, the system captures interaction events and computes an interaction metric comprising a dwell-time metric. In various embodiments, interaction events include one or more of cursor-position events, pointer-movement events, click events, keystroke events, scrolling events, viewport-focus events, window-focus events, touch-input events, and/or other interaction events generated during presentation of the stimulus. The dwell-time metric may be computed based on the event data and timing information associated with stimulus presentation (e.g., stimulus onset/offset and/or response-window boundaries). In certain embodiments, the dwell-time metric is computed without expressly prompting the participant to provide dwell-time values. In some embodiments, the dwell-time metric may be associated with the stimulus as a whole and/or a defined region-of-interest associated with the stimulus (e.g., using region metadata).

In accordance with certain aspects of the present disclosure, at step 310, the system receives a participant response during the response window. In various embodiments, the participant response comprises a classification selection, rating input, or other response input, and the response capture module associates the response with the stimulus ID (and optionally with the stimulus category). In certain embodiments, the system records timing information associated with the response, such as a response timestamp and/or response time measured relative to stimulus onset or response-window start. At decision step 312, the system determines whether the response was received within the response window. If the response was not received within the response window, the system records a missing or late response at step 314. In some embodiments, recording a missing/late response includes storing a validity indicator, rejecting the response, storing the response with a late flag, and/or storing a null response value, while still preserving the stimulus ID, timestamps, and any interaction metrics captured during presentation.

In accordance with certain aspects of the present disclosure, at step 316, the system stores a per-stimulus record. In various embodiments, the per-stimulus record includes the stimulus ID, stimulus category tag(s), the participant response (or a missing/late indicator), one or more timing values (e.g., stimulus onset/offset timestamps, response timestamp, response time), one or more interaction metrics (e.g., dwell-time metric and/or ROI dwell-time metric), and optionally summaries of captured interaction event data. The per-stimulus record may be stored in memory and/or non-transitory storage for later aggregation and metric computation. At decision step 318, the system determines whether additional stimuli remain to be presented in the session. If additional stimuli remain, method 300 returns to step 304 to select the next visual stimulus. If no additional stimuli remain, the system generates and stores an output record at step 320.

In various embodiments, generating and storing the output record may include one or more steps or operations for computing category-segmented metrics based on the per-stimulus records, such as per-category accuracy, per-category error rates, per-category response distributions, per-category dwell-time statistics, and/or per-category response-time statistics, and storing such metrics in a machine-readable output record. In certain embodiments, the output record may further include session metadata (e.g., timing parameters, stimulus identifiers presented, stimulus ordering) and may be stored and/or exported in a structured format for downstream processing.

Figure 4:
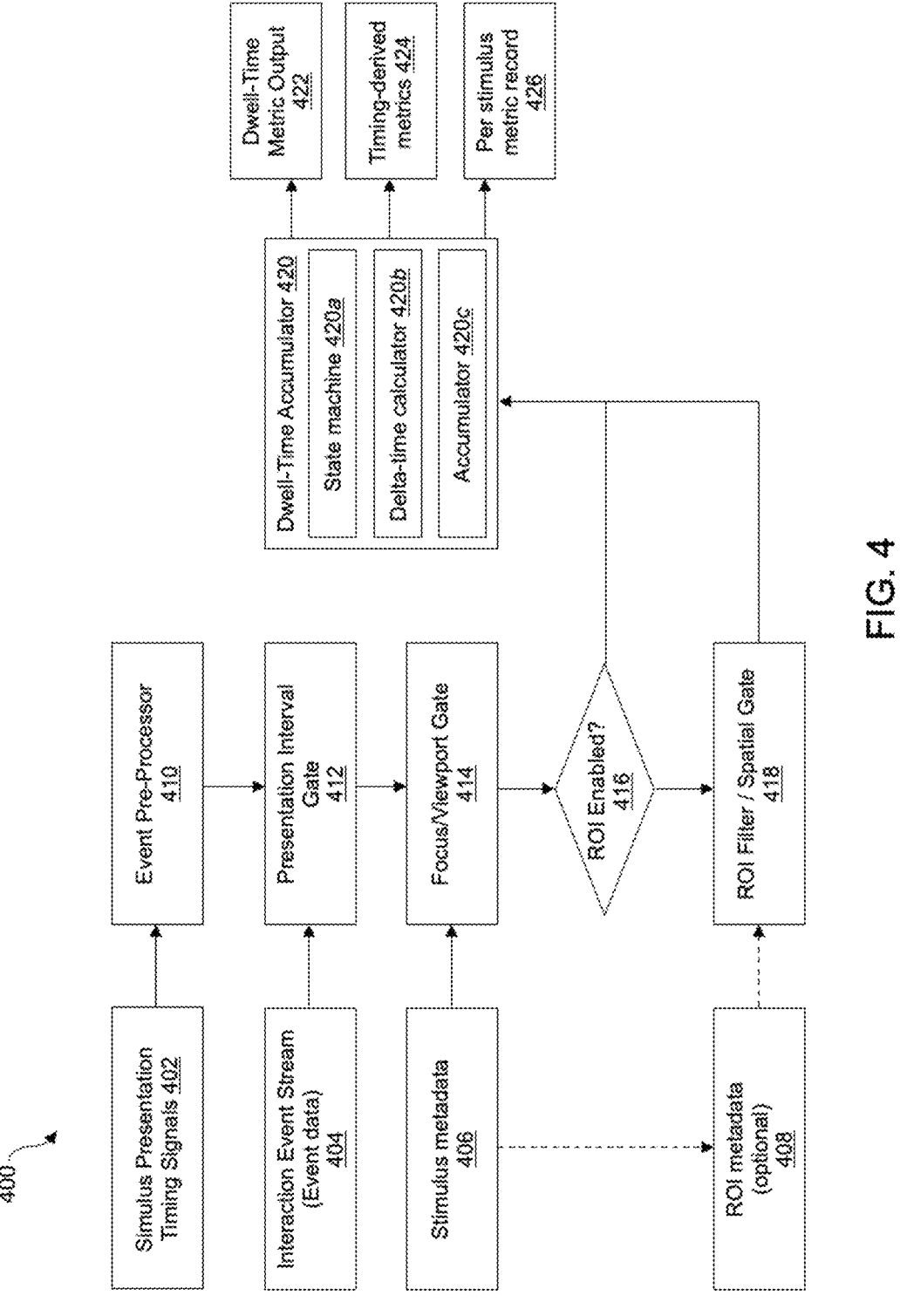
FIG. 4 is a block diagram illustrating an example process for computing dwell-time metrics from interaction event data and stimulus timing information.

Referring now to FIG. 4, a block diagram illustrating an example process flow 400 for computing one or more dwell-time metrics associated with a presented visual stimulus and/or a region-of-interest of the visual stimulus is shown. In accordance with certain aspects of the present disclosure, process flow 400 receives stimulus presentation timing signals 402, an interaction event stream (event data) 404, stimulus metadata 406, and (optionally) ROI metadata 408. In various embodiments, the stimulus presentation timing signals 402 include one or more timestamps and/or timing boundaries associated with presentation of a stimulus, such as a stimulus onset time, stimulus offset time, presentation interval boundaries, and/or response-window boundaries. The interaction event stream 404 may include time-stamped interaction events captured during participant interaction with the system, including, by way of example, cursor-position events, pointer-movement events, click events, keystroke events, scrolling events, viewport-focus events, window-focus events, touch-input events, and/or other interaction events. The stimulus metadata 406 may include a stimulus identifier and associated tags or attributes usable to associate event data and computed metrics with a particular stimulus and/or stimulus category. The optional ROI metadata 408 may define one or more regions-of-interest associated with a stimulus, for example by coordinates, bounding boxes, masks, or other region definition parameters.

In accordance with certain aspects of the present disclosure, an event pre-processor 410 receives the interaction event stream 404 and, in some embodiments, performs one or more pre-processing operations prior to dwell-time computation, including timestamp normalization, filtering of duplicate or invalid events, ordering or batching of events, and/or transformation of raw events into a normalized event representation. Following pre-processing, a presentation interval gate 412 filters and/or gates the pre-processed events based on the stimulus presentation timing signals 402 such that event data occurring outside of a defined stimulus presentation interval is excluded from subsequent dwell-time computation. In certain embodiments, a focus/viewport gate 414 further filters the event data based on window focus, viewport visibility, and/or other display state conditions such that event data is considered valid for dwell-time computation when the stimulus is actively viewable (e.g., when the application window is in focus or when the stimulus viewport is visible).

In accordance with certain embodiments, at decision block 416, process flow 400 may comprise one or more steps or operations for determining whether ROI-based processing is enabled for the current stimulus (e.g., whether ROI metadata 408 is available and/or an ROI option is enabled). If ROI-based processing is enabled, an ROI filter/spatial gate 418 filters the gated event data based on the ROI metadata 408 to identify ROI-qualified events (e.g., events having coordinates that intersect a defined region-of-interest). If ROI-based processing is not enabled, the event data may bypass the ROI filter/spatial gate 418 and be used to compute dwell time associated with the stimulus as a whole and/or an overall display region.

In accordance with certain embodiments, a dwell-time accumulator 420 computes one or more dwell-time metrics from the gated event data and the stimulus presentation timing signals 402. In the illustrated embodiment, the dwell-time accumulator 420 includes a state machine 420a, a delta-time calculator 420b, and an accumulator 420c. The state machine 420a may maintain one or more states indicative of whether events correspond to valid attention or interaction conditions (e.g., active vs. inactive). The delta-time calculator 420b may compute elapsed time values ($\Delta t$) between successive time-stamped events, bounded by the timing boundaries indicated by the stimulus presentation timing signals 402. The accumulator 420c may sum elapsed time values that satisfy the applicable gating conditions (e.g., within the presentation interval, within a focus/viewport condition, and optionally within an ROI) to produce one or more dwell-time metrics. In certain embodiments, the dwell-time computation is performed without expressly prompting the participant to provide dwell-time values, and instead is derived from the interaction event stream 404 and timing signals 402.

In accordance with certain aspects of the present disclosure, process flow 400 outputs a dwell-time metric output 422, which may include one or more dwell-time values associated with the stimulus and/or one or more ROIs. In certain embodiments, process flow 400 may further output timing-derived metrics 424, such as response time, latency to first interaction, counts of focus transitions, event counts, and/or other timing-related measures derived from the event stream and timing signals. Process flow 400 may also generate a per-stimulus metric record 426 that stores the computed dwell-time metric(s) and optional timing-derived metrics in association with the corresponding stimulus identifier and/or other metadata, for use in downstream category segmentation, metric computation, normalization, and/or output record generation.

In other embodiments, the dwell-time computation module may compute additional or alternative dwell-related metrics. In certain embodiments, the dwell-time computation module (e.g., dwell-time computation module 210)

computes one or more supplemental dwell-time metrics in addition to, or instead of, an accumulated Δt dwell-time value. For example, the system may compute (i) a latency-to-first-interaction metric indicative of a time between stimulus onset and a first qualifying interaction event, (ii) a latency-to-first-ROI-intersection metric indicative of a time between stimulus onset and a first interaction event intersecting a defined region-of-interest, and/or (iii) event-density metrics, such as counts or rates of interaction events within a stimulus interval or within a region-of-interest.

In certain embodiments, qualifying event data for dwell-time computation is determined using one or more thresholds applied to interaction characteristics. By way of example, a qualifying dwell segment may be identified when a cursor remains within a predetermined distance threshold for at least a threshold duration (cursor "hover"), when a cursor velocity remains below a velocity threshold for at least a threshold duration, and/or when touch contact or touch movement remains within a defined spatial tolerance. Additionally or alternatively, the system may treat time periods exceeding an inactivity threshold (e.g., no interaction events for a threshold duration) as non-qualifying for dwell-time accumulation or may assign such periods a reduced weight. Such thresholds may be applied globally or may be applied on an ROI-specific basis using region metadata.

In certain embodiments, the system generates an attention map for a stimulus from the interaction event stream. For example, the system may bin interaction events into spatial bins (e.g., a grid over a stimulus display area) and compute a heatmap representing event density and/or dwell-weighted event density across the stimulus. In some embodiments, heatmaps may be computed for the stimulus as a whole and/or separately for one or more ROIs, and summary values derived from such heatmaps (e.g., concentration measures, entropy, peak-bin values, or ROI-to-non-ROI ratios) may be stored as dwell-related metrics in association with a stimulus identifier.

In certain embodiments, dwell-time computation incorporates gating conditions and/or generates session-quality indicators. For example, the system may exclude, reduce, or separately report dwell-time contributions occurring when the application window is not in focus or when a stimulus viewport is not visible, and may store counts of focus transitions and/or other gating-related values as timing-derived metrics. The system may additionally store dwell-time validity flags indicating whether dwell-time metrics were computed using ROI processing or using whole-stimulus processing for a given stimulus.

Figure 5:
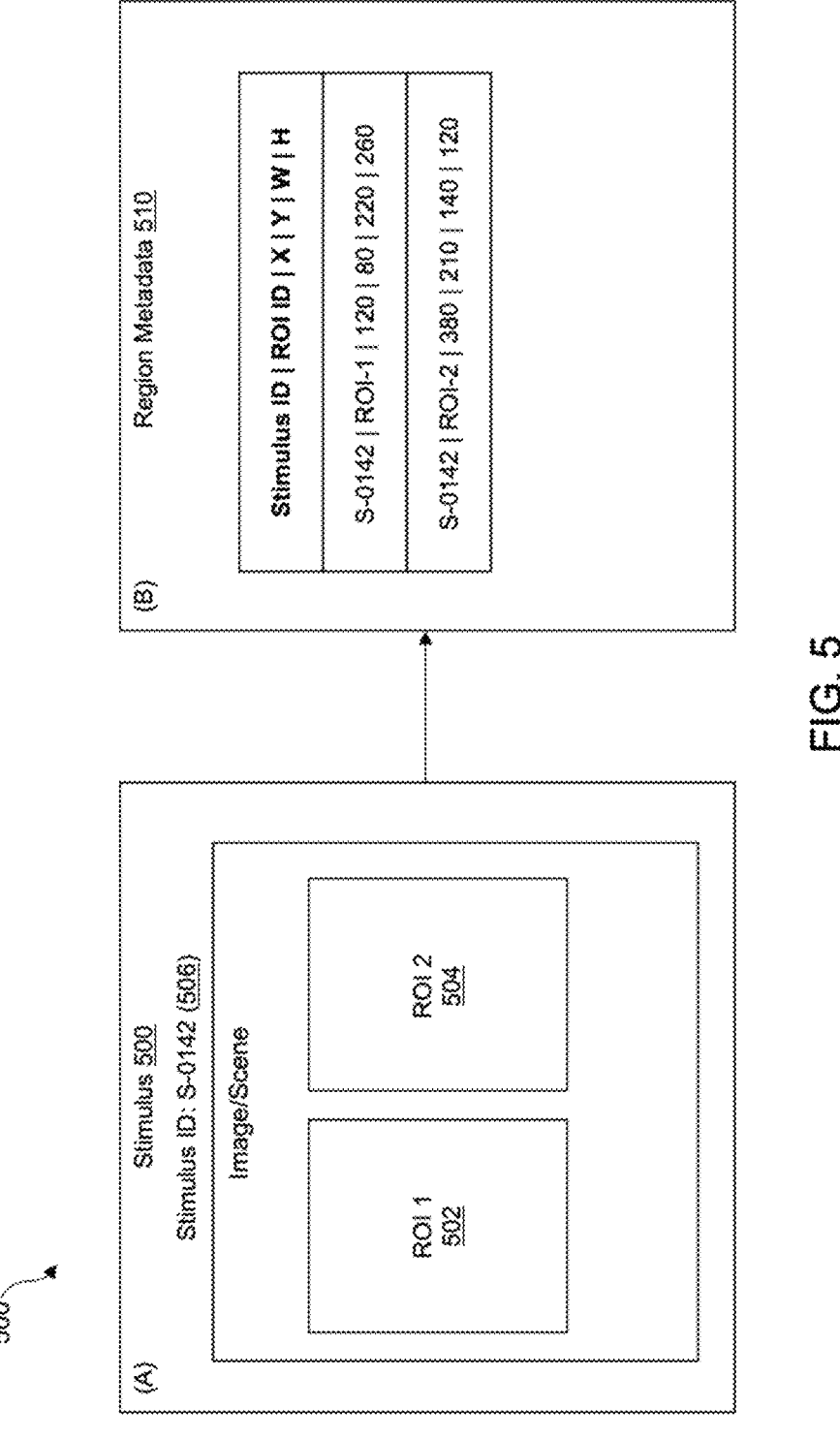
FIG. 5 is an illustrative diagram showing an example visual stimulus and one or more regions-of-interest defined by region metadata associated with a stimulus identifier.

Referring now to FIG. 5, an illustrative diagram showing an example visual stimulus 500 and one or more regions-of-interest (ROIs) defined for the stimulus is shown. In the illustrated embodiment, FIG. 5 includes a first panel (A) depicting the stimulus 500 (e.g., an image or scene) presented by a computerized behavioral testing system, and a second panel (B) depicting example region metadata 510 associated with the stimulus. As shown in panel (A), the stimulus 500 is associated with a stimulus identifier 506 (e.g., "Stimulus ID: S-0142"), which may be used to associate participant responses, interaction event data, and computed metrics with the corresponding stimulus. Panel (A) further illustrates a first region-of-interest 502 (ROI 1) and a second region-of-interest 504 (ROI 2) defined with respect to the displayed stimulus 500. In various embodiments, an ROI may correspond to any defined portion of the stimulus or display area for which interaction metrics are separately computed, such as a bounding box around a portion of the image, a polygonal region, a mask, or other region definition.

Panel (B) illustrates example region metadata 510 that defines the ROIs for the stimulus 500 in association with the stimulus identifier 506. In the illustrated example, the region metadata 510 includes entries for ROI-1 and ROI-2 keyed to the stimulus ID (S-0142), and further includes region definition parameters (e.g., X, Y, W, H) that specify ROI boundaries, such as coordinates and dimensions of bounding boxes corresponding to ROI 1 and ROI 2. In certain embodiments, the region metadata 510 may be stored in a stimulus repository and retrieved at runtime when the corresponding stimulus 500 is selected for presentation. In various embodiments, the region metadata 510 is provided to an interaction-metric computation module (e.g., a dwell-time computation module) to enable computation of ROI-specific dwell-time metrics. For example, interaction event data captured during presentation of the stimulus 500 (e.g., pointer, touch, viewport, focus, or other interaction events) may be evaluated relative to the region definition parameters in the region metadata 510 to identify events that correspond to a given ROI, and dwell time may be computed for ROI 1 and/or ROI 2 separately from (or in addition to) dwell time computed for the stimulus as a whole.

Figure 6:
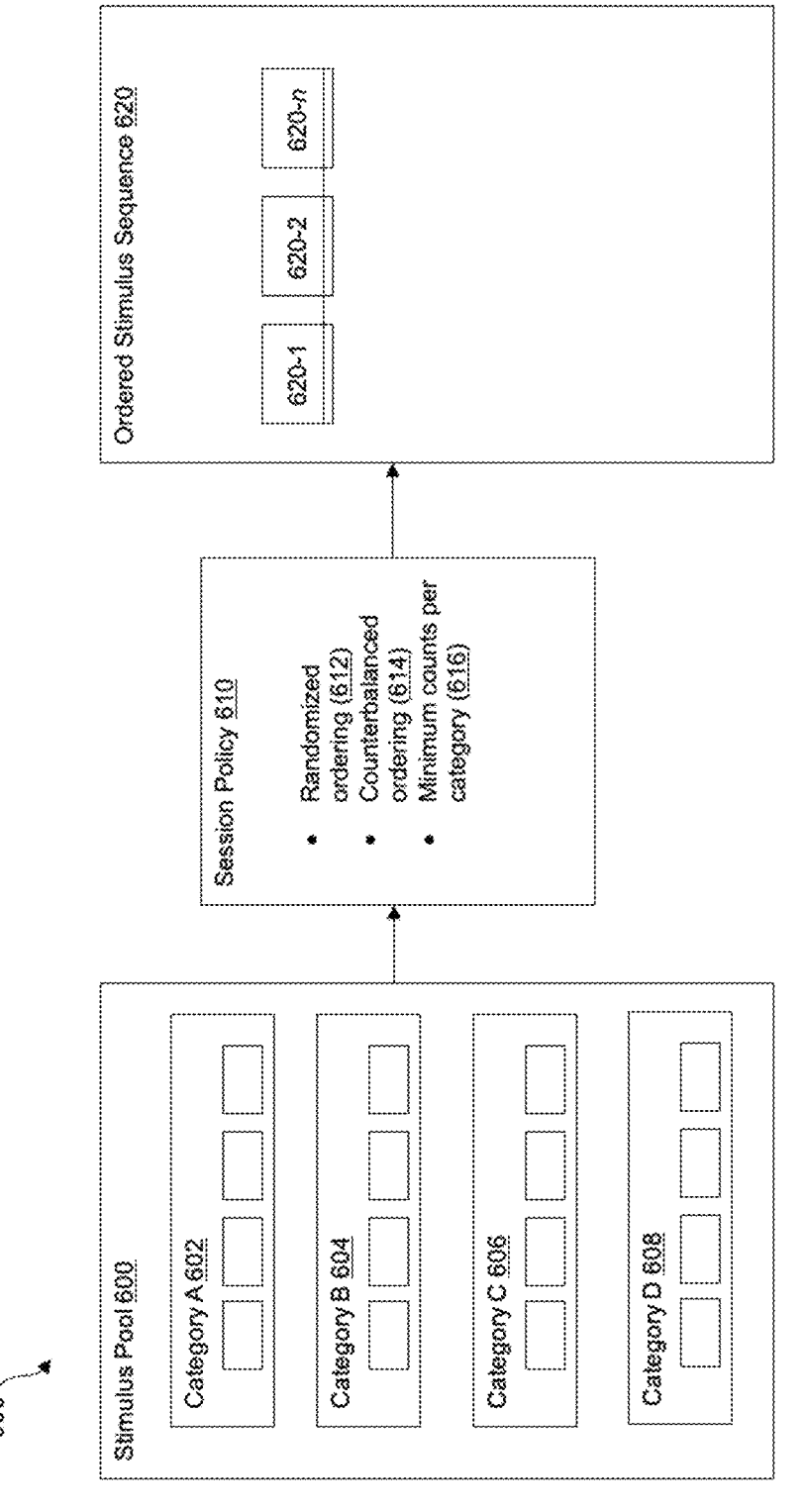
FIG. 6 is an illustrative diagram showing selection and ordering of a sequence of visual stimuli according to a session policy.

Referring now to FIG. 6, an illustrative diagram showing selection and ordering of a sequence of stimuli according to a session policy is shown. In accordance with certain aspects of the present disclosure, a stimulus pool 600 includes multiple stimuli that may be stored in, or retrieved from, a stimulus repository and grouped into respective stimulus categories, shown as Category A 602, Category B 604, Category C 606, and Category D 608. In accordance with certain embodiments, each stimulus in the stimulus pool 600 may be associated with a stimulus identifier and one or more stimulus category tags. In various embodiments, the stimulus category tags may correspond to any defined grouping used for segmentation and analysis, such as scenario groupings, stimulus attribute groupings, response-class groupings, demographic-tag groupings, or other category definitions specified for a given deployment or session. The categories shown in FIG. 6 are illustrative and not limiting.

In accordance with certain aspects of the present disclosure, a session policy 610 is applied to the stimulus pool 600 to determine an ordered stimulus sequence 620 for presentation during a testing session. In various embodiments, the session policy 610 comprises one or more ordering constraints and/or parameters that may be enforced by a session orchestrator. For example, the session policy 610 may specify randomized ordering 612 in which at least a portion of the stimuli are selected and/or ordered according to a random or pseudo-random process. In some embodiments, the session policy 610 further specifies counterbalanced ordering 614 across stimulus categories such that the resulting ordered stimulus sequence 620 balances category exposure, for example by limiting consecutive repetitions of a given category, distributing categories more uniformly across the session timeline, and/or balancing presentation positions of categories across different sessions or different participants. In some embodiments, the session policy 610 further specifies minimum counts per category 616 to ensure that at least a predetermined number of stimuli from each category 602-608 is included in the ordered stimulus sequence 620.

In accordance with certain aspects of the present disclosure, the application of the session policy 610 yields the ordered stimulus sequence 620, which in the illustrated embodiment includes an ordered set of stimuli 620-1, 620-2, through 620-*n*. In certain embodiments, the ordered stimulus sequence 620 includes, for each stimulus entry, the stimulus identifier and the associated stimulus category tag(s), such that the ordered sequence 620 may be provided to a presentation engine for controlled presentation of the stimuli and to downstream modules for category-based segmentation and metric computation. In certain embodiments, the ordered stimulus sequence 620 may be generated prior to session start (e.g., as a precomputed schedule), while in other embodiments the ordered stimulus sequence 620 may be generated dynamically during the session (e.g., selecting the "next" stimulus in view of policy constraints and already-presented stimuli). Although FIG. 6 depicts four example categories and three example policy features, it will be appreciated that any number of stimulus categories and any combination of ordering rules or constraints may be used without departing from the scope of the present disclosure.

In certain embodiments, a "stimulus identifier" comprises an opaque or arbitrary identifier (e.g., an alphanumeric value) that uniquely identifies a stimulus, and one or more stimulus attributes (including demographic attributes) are stored as separate metadata associated with the stimulus identifier. For example, the system may associate a stimulus identifier with one or more characteristic tags and/or metadata fields describing predetermined characteristics of a depicted subject (e.g., demographic attributes and/or non-demographic attributes), without requiring that any particular attribute be embedded in, or constitute, the stimulus identifier itself. In these embodiments, participant responses and interaction metrics may be recorded in association with the stimulus identifier, while category segmentation and analysis may be performed using one or more metadata fields linked to the identifier.

In certain embodiments, a stimulus is associated with multiple stimulus category tags, and category segmentation may be performed with respect to one tag, multiple tags, or combinations of tags. By way of example, a single stimulus may be tagged with (i) a demographic-tag category, (ii) a scenario-tag category (e.g., environment, context, presence of an object), (iii) a response-class grouping category, and/or (iv) a task-specific grouping category. When multiple category tags are present, the system may apply a priority rule, a hierarchical rule, or a multi-dimensional grouping operation to generate category-segmented metrics for one or more analysis dimensions.

In certain embodiments, a "level of threat" category is one example of a stimulus category label used for response capture and analysis; however, stimulus categories need not be limited to threat-class categories. For example, stimulus categories may correspond to scenario groupings, stimulus attribute groupings, demographic-tag groupings, lighting or setting groupings, presence or absence of an object, age-band groupings, facial-expression groupings, weapon-present/weapon-absent groupings, or other category definitions specified for a given deployment or session. Accordingly, the system may segment and compute metrics using one or more categories that are orthogonal to, or independent of, the participant's explicit response classes.

In certain embodiments, capturing a participant response "associated with" a stimulus identifier includes associating the participant response with the presented stimulus via the stimulus identifier and/or via metadata linked to the stimulus identifier. For example, the response may be stored in a per-stimulus record keyed by the stimulus identifier, while one or more stimulus attributes used for segmentation are stored as linked metadata such that downstream processing can segment responses and interaction metrics based on the linked attributes without requiring that the attributes be part of the response record key.

Figure 7:
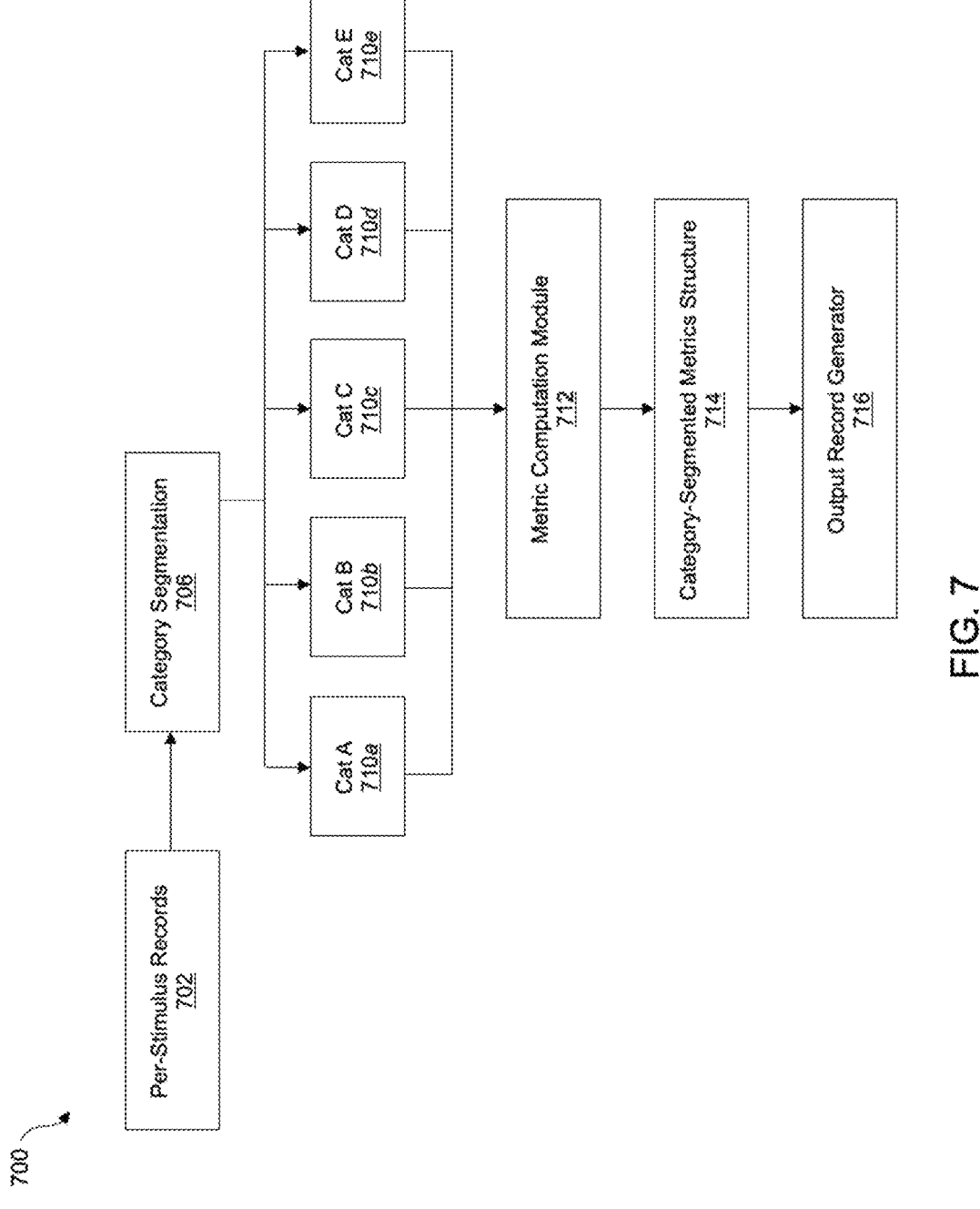
FIG. 7 is a block diagram illustrating generation of category-segmented response metrics from per-stimulus records.

Referring now to FIG. 7, a block diagram illustrating generation of category-segmented response metrics from per-stimulus records is shown. In accordance with certain aspects of the present disclosure, per-stimulus records 700 are provided to a category segmentation module 702. The per-stimulus records 700 may be generated during administration of a testing session (e.g., as described with respect to FIG. 3) and stored in memory and/or non-transitory storage. In various embodiments, each per-stimulus record includes a stimulus identifier and one or more stimulus category tags, and further includes one or more of: a participant response (or an indicator of a missing/late/invalid response), a response timestamp and/or response time, a dwell-time metric (including an ROI dwell-time metric where applicable), event-derived counts or summaries, and/or other timing-derived values.

In accordance with certain aspects of the present disclosure, the category segmentation module 702 partitions the per-stimulus records 700 into category-specific datasets based on the stimulus category tags. In the illustrated example, the category-specific datasets include Cat A 710*a*, Cat B 710*b*, Cat C 710*c*, Cat D 710*d*, and Cat E 710*e*. In certain embodiments, the category segmentation module 702 assigns each per-stimulus record to exactly one category dataset when a single category tag is used. In other embodiments, a per-stimulus record may be assigned to multiple category datasets when multiple category tags are used (e.g., where a stimulus is tagged with multiple attributes), or the per-stimulus record may be assigned according to a priority rule. In certain embodiments, the category segmentation module 702 may also perform one or more pre-processing operations prior to metric computation, such as filtering records marked invalid, separating missing/late responses, and/or normalizing record fields into a consistent internal format.

In accordance with certain aspects of the present disclosure, the category-specific datasets 710*a*-710*e* are provided to a metric computation module 712, which computes one or more category-segmented response metrics for the participant and/or session. In various embodiments, the metric computation module 712 computes, for each category, one or more of: accuracy measures, error rates, response distributions across allowed response classes, response-time statistics (e.g., mean, median, variance, percentiles), dwell-time statistics (e.g., mean, median, variance, percentiles for whole-stimulus dwell time and/or ROI dwell time), and/or other timing-derived or interaction-derived statistics derived from the per-stimulus records. In certain embodiments, the metric computation module 712 computes category-level summary metrics from both (i) the participant responses and (ii) the interaction metrics, such that category-segmented performance can be represented as a structured set of quantitative values.

In accordance with certain aspects of the present disclosure, the metric computation module 712 outputs a category-segmented metrics structure 714 that stores the computed metrics in a machine-readable representation organized by category. In certain embodiments, the category-segmented metrics structure 714 comprises a data structure (e.g., a map, table, or array) with entries keyed by category, each entry including one or more computed metrics for that category. The category-segmented metrics structure 714 is provided to an output record generator 716 for inclusion in a machine-readable output record (e.g., as described with respect to FIG. 11). In certain embodiments, the category-segmented metrics structure 714 may additionally be provided to downstream processing modules, such as a participant-specific normalization module, for generation of participant-specific normalized metrics based on comparisons among category-segmented metrics for the same participant.

Figure 8:
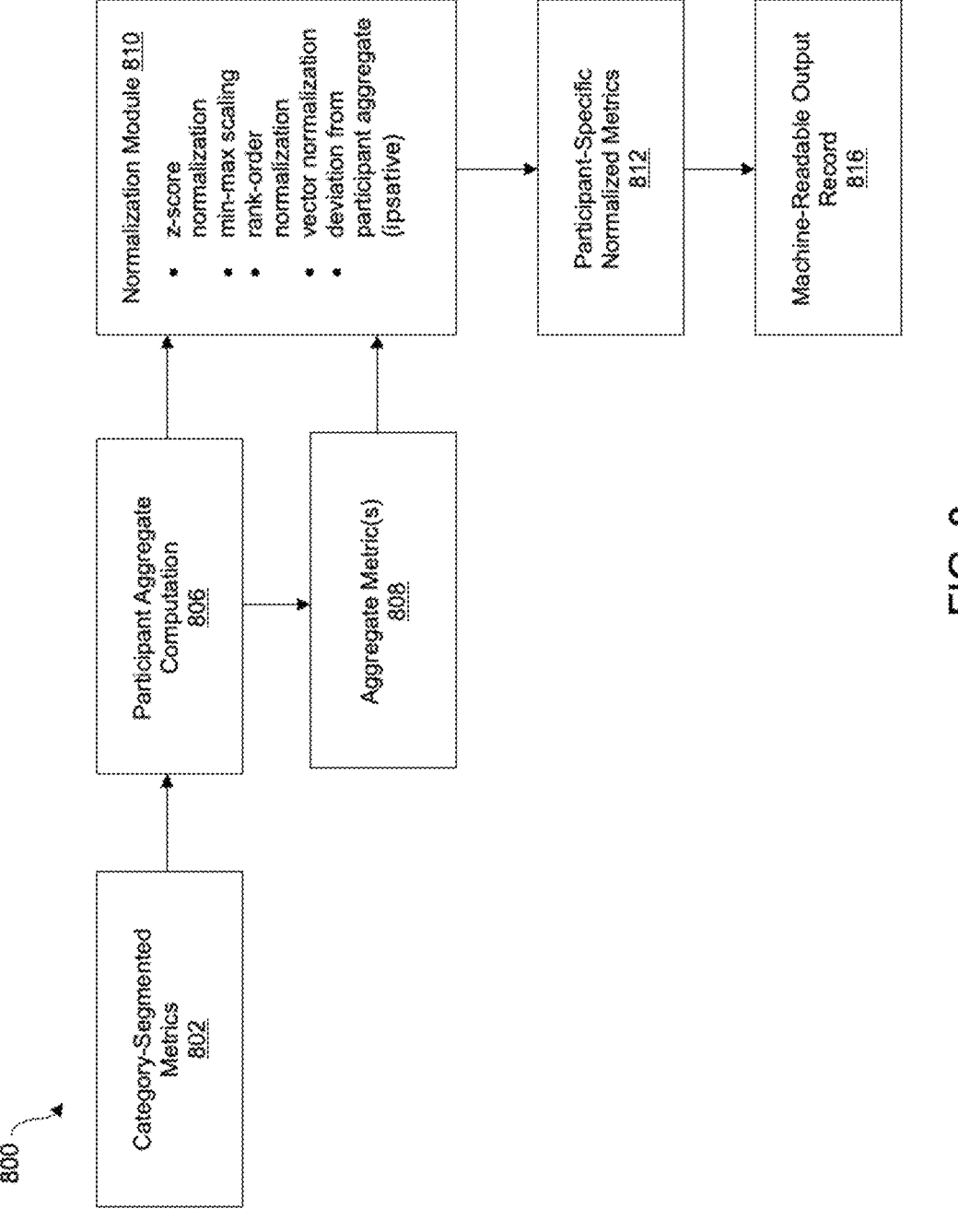
FIG. 8 is a block diagram illustrating participant-specific normalization of category-segmented response metrics to produce participant-specific normalized metrics.

Referring now to FIG. 8, a block diagram illustrating participant-specific normalization of category-segmented response metrics to produce participant-specific normalized metrics for inclusion in a machine-readable output record is shown. In the illustrated embodiment, category-segmented metrics 800 (e.g., as generated as described with respect to FIG. 7) are provided as input for processing on a participant basis. In various embodiments, the category-segmented metrics 800 comprise one or more metric values computed for each of multiple stimulus categories for a given participant, such as category-specific accuracy, error rate, response distribution statistics, dwell-time statistics, and/or response-time statistics. The category-segmented metrics 800 are provided to a participant aggregate computation module 802, which computes one or more aggregate metric(s) 806 based on the category-segmented metrics 800 for the same participant.

In accordance with certain aspects of the present disclosure, the participant aggregate computation module 802 computes an aggregate metric 806 by combining category-level metrics across multiple categories for a given metric type (e.g., computing an overall average accuracy across categories, an overall dwell-time baseline, or an overall response-time baseline). The aggregate metric(s) 806 may comprise one or more of an average, median, weighted combination, vector baseline, composite metric, or other reference value computed from the participant's own category-level metrics. In certain embodiments, the participant aggregate computation module 802 may compute separate aggregate metrics 806 for different metric types (e.g., one aggregate for accuracy-related metrics and another aggregate for timing-related metrics). The category-segmented metrics 800 and the aggregate metric(s) 806 are provided to a normalization module 810. The normalization module 810 generates participant-specific normalized metrics 812 by performing one or more normalization operations that compare metrics across categories for the same participant and/or compare category-level metrics to the aggregate metric(s) 806 for that participant. In certain embodiments, the normalization module 810 may generate an ipsative metric by computing a deviation of a category-level metric from a participant aggregate metric 806 (e.g., difference, residual, or other distance measure) such that the resulting normalized values represent within-participant differences across categories. Additionally or alternatively, the normalization module 810 may implement one or more other normalization techniques, including z-score normalization, min-max scaling, rank-order normalization, and/or vector normalization, applied across category-level metrics for the same participant.

In accordance with certain aspects of the present disclosure, the participant-specific normalized metrics 812 may be represented as a participant-specific output vector or category-keyed data structure in which each category is associated with one or more normalized values, and such normalized values may be generated for one or more metric types (e.g., accuracy-related, error-rate, dwell-time, and/or response-time metrics). The participant-specific normalized metrics 812 are provided for inclusion in a machine-readable output record 816. In certain embodiments, the output record

816 may store both the participant-specific normalized metrics 812 and the underlying category-segmented metrics 800 and may further include session metadata and/or other computed metrics, and may be stored and/or exported in a structured format for downstream processing by an external computing system.

In certain embodiments, the system applies calibration or normalization operations based on session metadata to reduce device-dependent variability. For example, the system may store display parameters (e.g., resolution, scaling, viewport dimensions) and/or device class identifiers in session metadata and may use such metadata to normalize one or more interaction metrics, such as dwell-time metrics, event-density metrics, and/or response-time metrics, to facilitate comparison across sessions executed on different device types or display configurations. In some embodiments, such calibration includes scaling spatial thresholds (e.g., ROI intersection tolerances, cursor-movement thresholds, spatial bin sizes) based on display scaling or viewport dimensions and/or scaling timing thresholds based on measured client performance characteristics (e.g., presentation timing drift) recorded in the session metadata.

In certain embodiments, the system applies one or more policies for handling missing, late, or invalid responses when computing category-segmented metrics and/or participant-specific normalized metrics. By way of example, the system may exclude invalid trials from category-level metric computation, separately compute metrics for valid trials and invalid trials, apply weights to trials based on validity indicators, and/or impute or substitute default values for missing responses in a manner specified by a session policy. In some embodiments, the output record stores validity statistics (e.g., counts of valid responses, late responses, and missing responses per category) and such statistics may be used to qualify interpretation of computed metrics and/or to enforce minimum valid-trial counts prior to generating one or more output metrics.

In certain embodiments, the system computes one or more reliability indicators to assess internal consistency of participant responses or metrics. For example, a session policy may specify that one or more stimuli are repeated within a session and/or across sessions, and the system may compute repeatability measures such as (i) agreement between responses to repeated stimuli, (ii) variance of response-time metrics across repeated presentations, and/or (iii) variance of dwell-time metrics or ROI dwell-time metrics across repeated presentations. In some embodiments, the system computes a test-retest consistency metric across multiple sessions for a participant, and stores such reliability indicators in the machine-readable output record.

In certain embodiments, participant-specific normalization is supplemented by additional baselining options. For example, the system may compute a session baseline metric for a participant (e.g., a baseline derived from a subset of stimuli or an aggregate across all categories) and normalize category-level metrics relative to such baseline. Additionally or alternatively, the system may compute device-class baselines (e.g., baselines corresponding to a device model, operating system, or display class) and apply device-class adjustments to one or more timing-derived metrics prior to generating participant-specific normalized outputs. In these embodiments, the output record may store both raw metrics and calibrated/normalized metrics along with associated baseline identifiers so that downstream systems can reproduce or audit the normalization.

Figure 9:
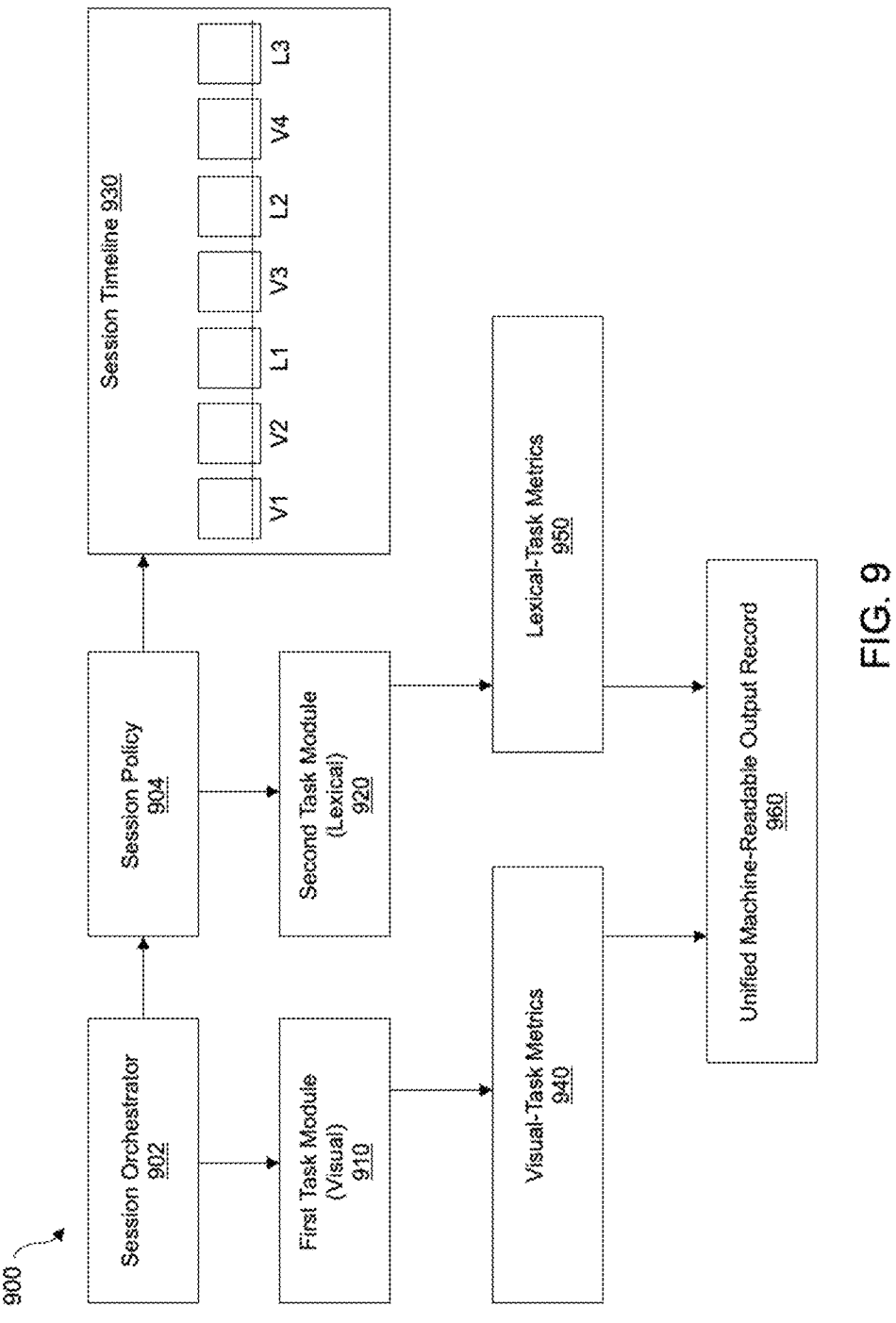
FIG. 9 is an illustrative diagram showing interleaved execution of multiple task modules within a session and generation of a unified output record.

Referring now to FIG. 9, an illustrative diagram showing interleaved execution of multiple task modules within a testing session and generation of a unified machine-readable output record is shown. In accordance with certain aspects of the present disclosure, a session orchestrator 902 controls execution of a session based on a session policy 904. The session policy 904 may specify one or more rules and/or parameters governing session administration, including, by way of example, ordering of trials, interleaving of different task modules, randomized and/or counterbalanced sequencing, minimum trial counts per module, and/or other session constraints. As shown in the illustrated embodiment, the session orchestrator 902 causes execution of a first task module (visual) 910 and a second task module (lexical) 920 during a session represented by a session timeline 930. In the illustrated example timeline 930, trials from the first task module 910 (shown as V1, V2, V3, V4) and trials from the second task module 920 (shown as L1, L2, L3) are interleaved within a single session.

In accordance with certain aspects of the present disclosure, the session orchestrator 902 may interleave trials according to the session policy 904, such that the sequence of visual and lexical trials may be alternated, mixed, grouped, or otherwise arranged while maintaining applicable timing and response constraints described elsewhere herein. The first task module 910 is configured to present scenario-based visual stimuli and capture corresponding participant responses and interaction metrics, from which visual-task metrics 940 are computed. In various embodiments, the visual-task metrics 940 may include category-segmented response metrics and associated timing-derived statistics, such as per-category accuracy, error rates, response distributions, response-time statistics, and/or dwell-time statistics. The second task module 920 is configured to present lexical stimuli (e.g., letter strings) and capture lexical-decision responses, from which lexical-task metrics 950 are computed. In various embodiments, the lexical-task metrics 950 include at least a lexical error rate and may include additional accuracy and/or timing-related measures. The visual-task metrics 940 and the lexical-task metrics 950 are combined to generate a unified machine-readable output record 960. In various embodiments, the unified machine-readable output record 960 stores a structured representation of participant performance across multiple task modules and may be stored in non-transitory storage and/or exported in a structured format for downstream processing by an external computing system.

Figure 10:
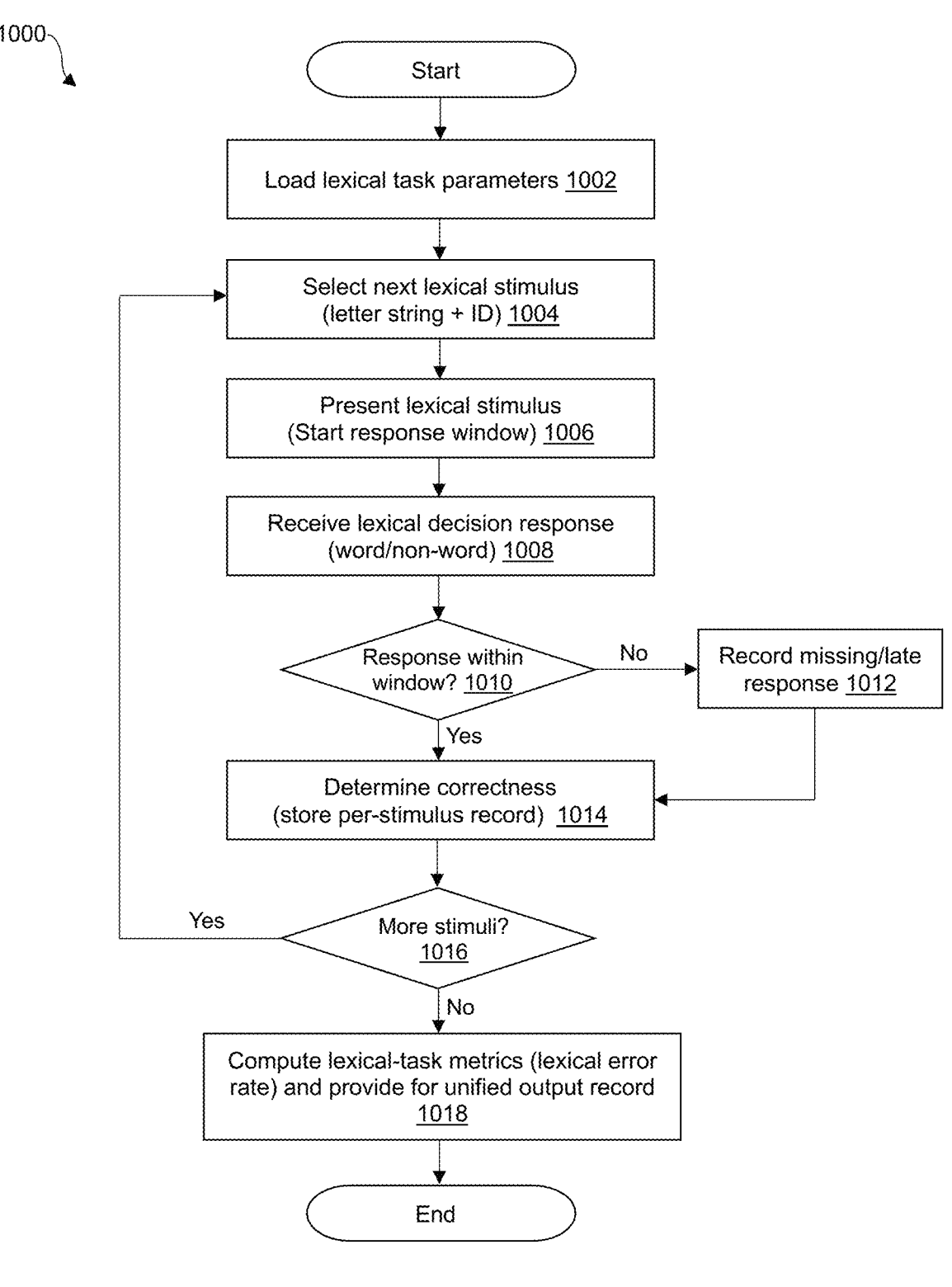
FIG. 10 is a flowchart illustrating an example method for operating a lexical task module.

Referring now to FIG. 10, a flowchart illustrating an example method 1000 for operating a lexical task module using a computerized behavioral testing system is shown. In accordance with certain aspects of the present disclosure, method 1000 may be executed by one or more processors executing instructions stored in memory and may be performed as part of a multi-module testing session (e.g., interleaved with a visual-stimulus task) or as a standalone lexical task.

In accordance with certain embodiments, method 1000 may be initiated upon executing one or more steps or operations for loading lexical task parameters at step 1002. In various embodiments, the lexical task parameters specify one or more administration settings, such as a response window duration, ordering rules for lexical stimuli (e.g., fixed, randomized, pseudo-randomized, or counterbalanced ordering), selection of one or more lexical stimulus sets, and/or permitted response classes. In certain embodiments, the lexical task parameters further specify one or more constraints for administering the lexical task, such as disabling stimulus replay or backtracking and/or rejecting responses outside of the response window. At step 1004, method 1000 may be configured to execute one or more steps or operations for selecting a next lexical stimulus for presentation. In the illustrated embodiment, the lexical stimulus comprises a letter string and an associated identifier (ID). In various embodiments, selecting the lexical stimulus includes retrieving the letter string and associated metadata from a lexical stimulus repository, where the metadata may include, for example, a ground-truth label indicating whether the letter string is a word or a non-word and, optionally, an identifier of a lexical stimulus set from which the letter string was selected.

At step 1006, method 1000 may be configured to execute one or more steps or operations for presenting the selected lexical stimulus on a display and initiates a response window during which participant responses are accepted. In certain embodiments, the system time-stamps lexical stimulus onset and/or response-window start and controls acceptance of input such that only responses received during the response window are considered valid. In some embodiments, enforcing the response window includes rejecting, ignoring, or flagging responses received outside of the response window and/or disabling interface actions that would permit a participant to replay or revisit the lexical stimulus. At step 1008, method 1000 may be configured to execute one or more steps or operations for receiving a lexical-decision response from the participant indicating whether the presented letter string is a word or a non-word. In certain embodiments, method 1000 records a response timestamp and/or computes a response time relative to stimulus onset and/or response-window start.

In accordance with certain embodiments, at decision step 1010, method 1000 may be configured to execute one or more steps or operations for determining whether the response was received within the response window. If the response was not received within the response window, method 1000 may execute one or more steps or operations for recording a missing or late response at step 1012. In various embodiments, recording a missing/late response includes storing a validity indicator, storing a null response value, and/or storing the received response with a late flag while preserving associated timing data. At step 1014, method 1000 may execute one or more steps or operations for determining correctness and stores a per-stimulus record for the lexical stimulus. In various embodiments, determining correctness includes comparing the received lexical-decision response to the ground-truth label for the letter string (word/non-word). The per-stimulus record may include, by way of example, the lexical stimulus ID, the presented letter string (or a reference thereto), the participant response (or a missing/late indicator), a correctness indicator, and timing information such as response time and/or response timestamp. In some embodiments, the per-stimulus record further includes a lexical stimulus set identifier when multiple lexical stimulus sets are used.

In accordance with certain aspects of the present disclosure, at decision step 1016, method 1000 may execute one or more steps or operations for determining whether additional lexical stimuli remain for presentation. If additional lexical stimuli remain, the method returns to step 1004 to select the next lexical stimulus. If no additional lexical stimuli remain, the system computes one or more lexical-task metrics at step 1018 and provides such metrics for inclusion in a unified machine-readable output record. In various embodiments, the lexical-task metrics include at least a lexical error rate based on incorrect lexical-decision responses across the lexical stimuli presented. In certain embodiments, the system may additionally compute one or more supplemental lexical metrics, such as overall accuracy, response-time statistics, and/or separate error rates or accuracy values for respective lexical stimulus sets, where applicable.

Figure 11:
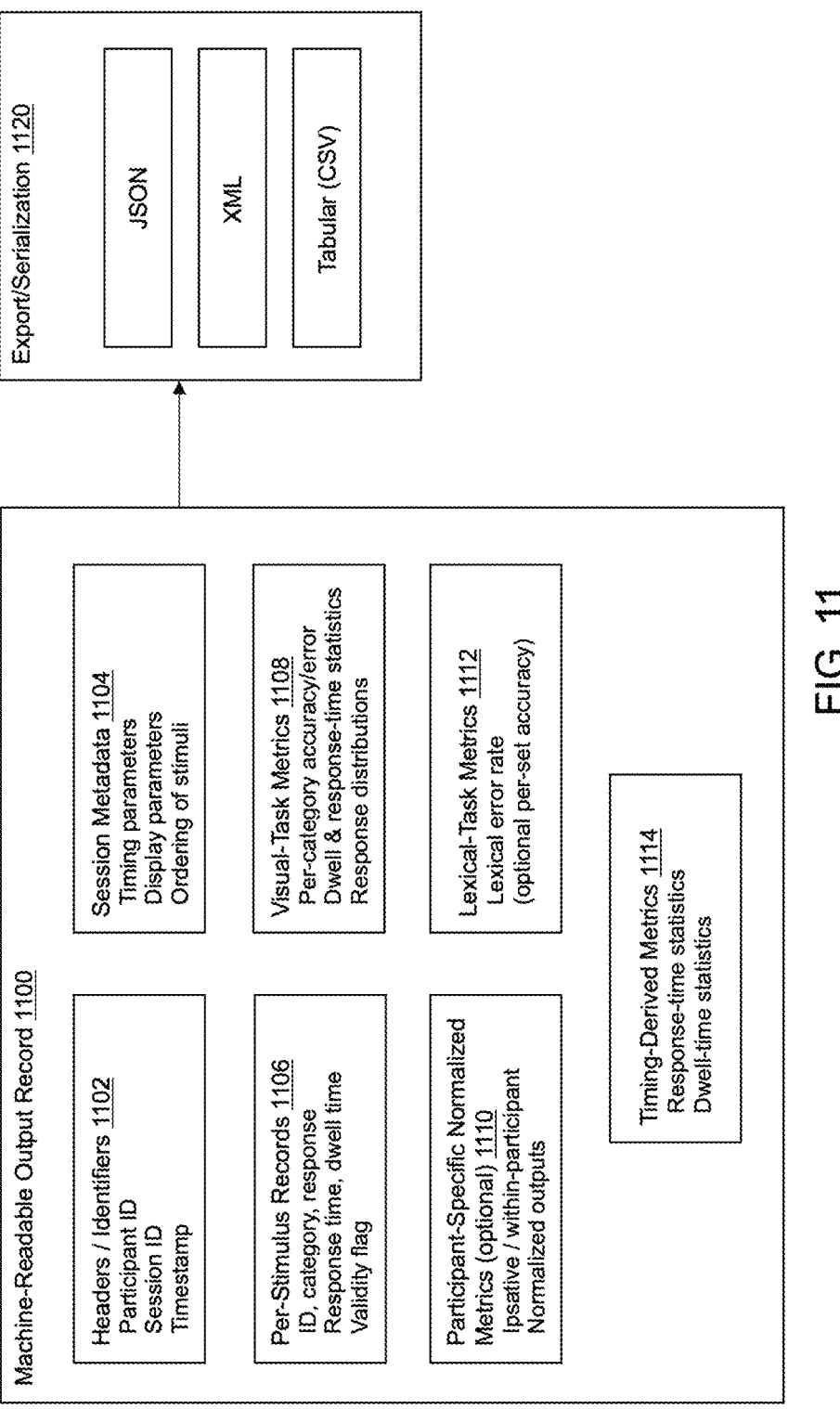
FIG. 11 is an illustrative diagram showing an example machine-readable output record and example export formats.

Referring now to FIG. 11, an illustrative diagram showing an example machine-readable output record 1100 generated by a computerized behavioral testing system is shown. In accordance with certain aspects of the present disclosure, the machine-readable output record 1100 is generated for a participant and/or testing session and stores a structured representation of results and computed metrics suitable for storage and/or export for downstream processing. As shown, the machine-readable output record 1100 includes headers/ identifiers 1102. In various embodiments, the headers/identifiers 1102 include one or more identifiers and/or timestamps, such as a participant identifier (Participant ID), a session identifier (Session ID), and a session timestamp (Timestamp). The machine-readable output record 1100 further includes session metadata 1104. In various embodiments, the session metadata 1104 includes one or more parameters or descriptors associated with administration of the session, such as timing parameters (e.g., presentation intervals, response windows, and/or other timing constraints), display parameters (e.g., resolution, scaling, or other display settings), and ordering of stimuli (e.g., identifiers of presented stimuli and/or a sequence representation indicating an order in which stimuli were presented).

In accordance with certain aspects of the present disclosure, the machine-readable output record 1100 further includes per-stimulus records 1106. In various embodiments, the per-stimulus records 1106 comprise a list or set of records generated for individual stimuli presented during the session. For example, a per-stimulus record may include a stimulus identifier, a stimulus category tag, a participant response (or a missing/late indicator), timing information such as response time, one or more interaction metrics such as dwell time (including ROI dwell time where applicable), and a validity flag indicating whether the response was valid (e.g., received within a response window). The machine-readable output record 1100 further includes visual-task metrics 1108. In various embodiments, the visual-task metrics 1108 include category-segmented response metrics such as per-category accuracy and/or error measures, dwell-time statistics and response-time statistics, and response distributions across allowed response classes.

In accordance with certain aspects of the present disclosure, the machine-readable output record 1100 optionally includes participant-specific normalized metrics 1110. In various embodiments, the participant-specific normalized metrics 1110 include ipsative or within-participant normalized outputs derived by comparing category-segmented metrics across categories for the same participant and/or by comparing category-level metrics to one or more participant aggregate metrics. In accordance with certain aspects of the present disclosure, the machine-readable output record 1100 further includes lexical-task metrics 1112. In various embodiments, the lexical-task metrics 1112 include at least a lexical error rate and may optionally include per-set accuracy when multiple lexical stimulus sets are used. The machine-readable output record 1100 further includes timing-derived metrics 1114. In various embodiments, the timing-derived metrics 1114 include response-time statistics and dwell-time statistics computed across the session and/or across stimuli. As further shown, the machine-readable output record 1100 may be provided for export/serialization 1120. In various embodiments, export/serialization 1120 includes exporting the output record 1100 in a structured format such as JSON, XML, or a tabular format (e.g., CSV) for storage, reporting, analytics, or other downstream processing by an external computing system.

In certain embodiments, the machine-readable output record (e.g., output record 1100) is generated and exported according to a defined schema so that downstream systems can reliably parse, validate, and audit stored results. By way of example and not limitation, the output record may be serialized in a structured format including JSON, XML, and/or a tabular format (e.g., CSV), and may include a schema version identifier and/or a record type identifier. In one non-limiting example, the output record is serialized as a JSON object including headers/identifiers, session metadata, per-stimulus records, visual-task metrics, optional participant-specific normalized metrics, lexical-task metrics, and timing-derived metrics. Table 1, shown below, illustrates a JSON snippet that may be generated in accordance with the principals of the present disclosure.

TABLE 1

Illustrative JSON snippet

```
{
 "schema_version": "1.0",
 "record_type": "unified_machine_readable_output_record",
 "headers": {
  "participant_id": "P12345",
  "session_id": "S67890",
  "timestamp_utc": "2026-02-06T14:03:22Z"
 },
 "session_metadata": {
  "device_identifier": "device_hash_or_id",
  "display_parameters": { "resolution": "1920x1080", "scaling": 1.0, "refresh_hz": 60 },
  "timing_parameters": { "presentation_interval_ms": 10000, "response_window_ms": 10000
 },
  "stimulus_order": ["V001","V002","V003","L001", "V004"]
 },
 "per_stimulus_records": [
  {
   "stimulus_id": "V001",
   "stimulus_category": "CatA",
   "response": "NoThreat",
   "response_time_ms": 1840,
   "dwell_time_ms": 5120,
   "roi_dwell_time_ms": { "ROI1": 2100, "ROI2": 980 },
```

TABLE 1-continued

| Illustrative JSON snippet |
| --- |

```
    "validity_flag": "valid"
  }
],
"visual_task_metrics": {
  "per_category_accuracy": { "CatA": 0.75, "CatB": 0.60 },
  "per_category_error_rate": { "CatA": 0.25, "CatB": 0.40 },
  "response_distributions":    {    "CatA":    {    "NoThreat":    10,    "PossibleThreat":    2,
"DangerousThreat": 1 } },
  "dwell time_statistics": { "CatA": { "mean_ms": 4800, "median_ms": 4600 } },
  "response_time_statistics": { "CatA": { "mean_ms": 1900, "median_ms": 1750 } }
},
"participant_specific_normalized_metrics": {
  "ipsative_deviation_from_aggregate": { "CatA": −0.10, "CatB": 0.12 }
},
"lexical_task_metrics": {
  "lexical_error_rate": 0.18,
  "per_set_accuracy": { "static_words": 1.00, "emotive_words": 1.00, "nonsense_words": 0.68
}
},
"timing_derived_metrics": {
  "overall_response_time_ms": { "mean": 1850, "median": 1725 },
  "overall_dwell_time_ms": { "mean": 4950, "median": 4700 }
}
}
```

In various embodiments, one or more fields shown above may be omitted, combined, renamed, represented by references, or organized into different nested structures, without departing from the scope of the present disclosure.

In certain embodiments, per-stimulus records are exported in a tabular format (e.g., CSV) in which each row corresponds to a stimulus presentation and each column corresponds to a schema-defined field. By way of example, a tabular export may include columns such as: participant_id, session_id, timestamp, stimulus_id, stimulus_category, response, response_time, dwell_time, ROI1_dwell_time, ROI2_dwell_time, validity_flag, and/or additional timing-derived or event-derived fields. In certain embodiments, category-segmented metrics and lexical-task metrics are exported as (i) separate tables/files, (ii) separate record types, or (iii) a header section plus one or more tabular sections.

In certain embodiments, the output record includes one or more reproducibility fields, such as a schema_version value, a session_policy identifier, a stimulus_set identifier, and/or hash values corresponding to a stimulus set, region metadata set, or software build identifier. In such embodiments, the system may store such reproducibility fields as part of session metadata to facilitate later validation, auditing, or replay of the computational steps that generated the metrics in the output record.

Referring now to FIGS. 12A-12F, example user interface (UI) screens 1200a-1200f presented by a computerized behavioral testing system during administration of a multi-part computerized test are shown. In various embodiments, the UI screens 1200a-1200f are rendered on a participant device display (e.g., a smartphone, tablet, laptop, or desktop display) and are configured to guide the participant through (i) a visual-stimulus threat assessment portion and (ii) a lexical decision portion of the test.

Figure 12A:
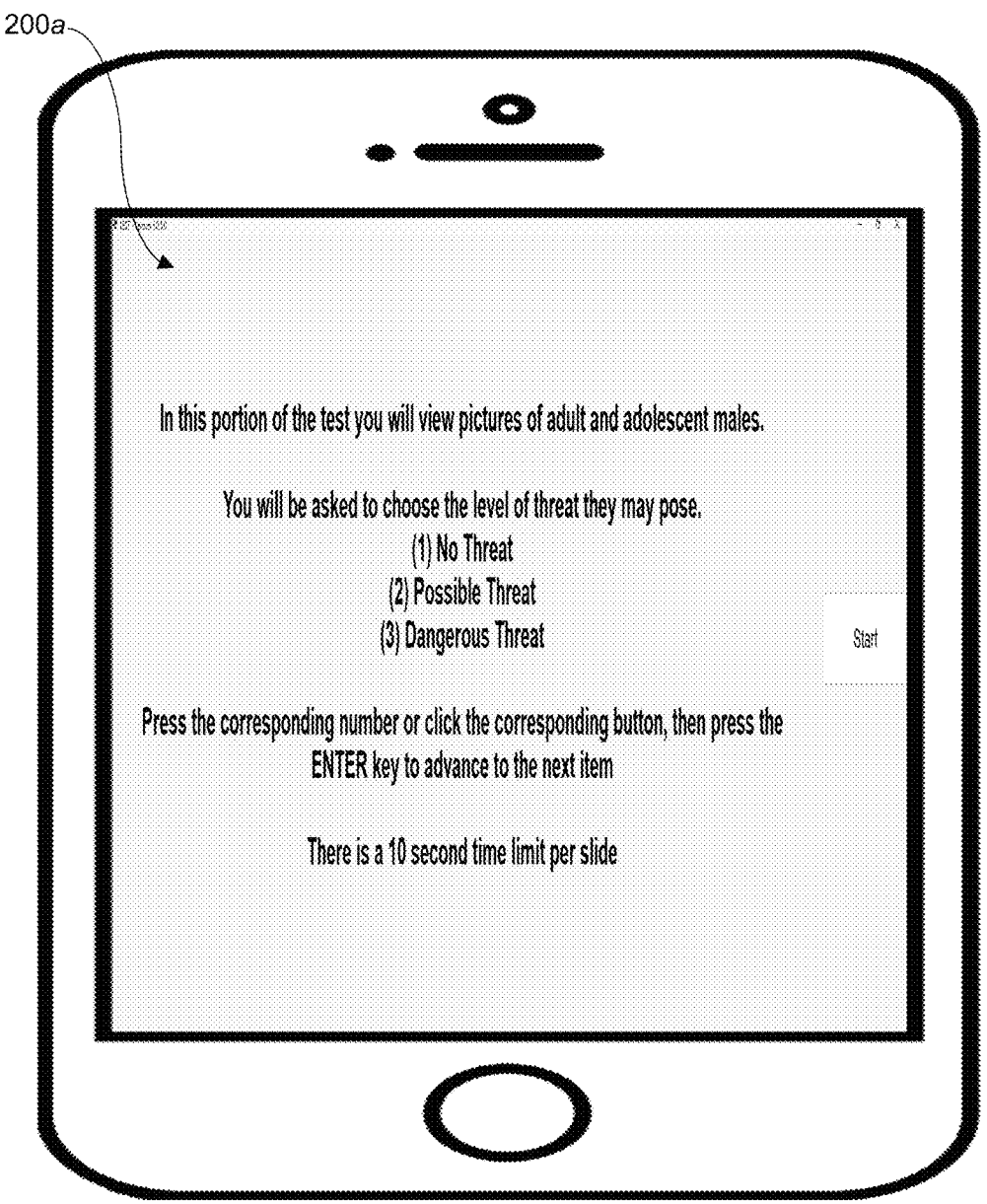
FIGS. 12A-12F are user interface diagrams of an exemplary computerized behavioral measurement and testing system, in accordance with certain aspects of the present disclosure.

FIG. 12A illustrates an example instructional UI screen 1200a for a threat assessment portion of the test. As shown, the instructional UI screen 1200a informs the participant that the participant will view pictures (e.g., of adult and adolescent males) and will be asked to choose a level of threat associated with each picture. In the illustrated embodiment, the permitted response classes include "(1) No Threat," "(2) Possible Threat," and "(3) Dangerous Threat," and the instructional UI screen 1200a provides instructions to input a response by pressing a corresponding number or clicking a corresponding button and then pressing an "ENTER" key to advance. In certain embodiments, the instructional UI screen 1200a further indicates a time limit per slide (e.g., 10 seconds) and provides a "Start" control to initiate the threat assessment portion.

Figure 12B:
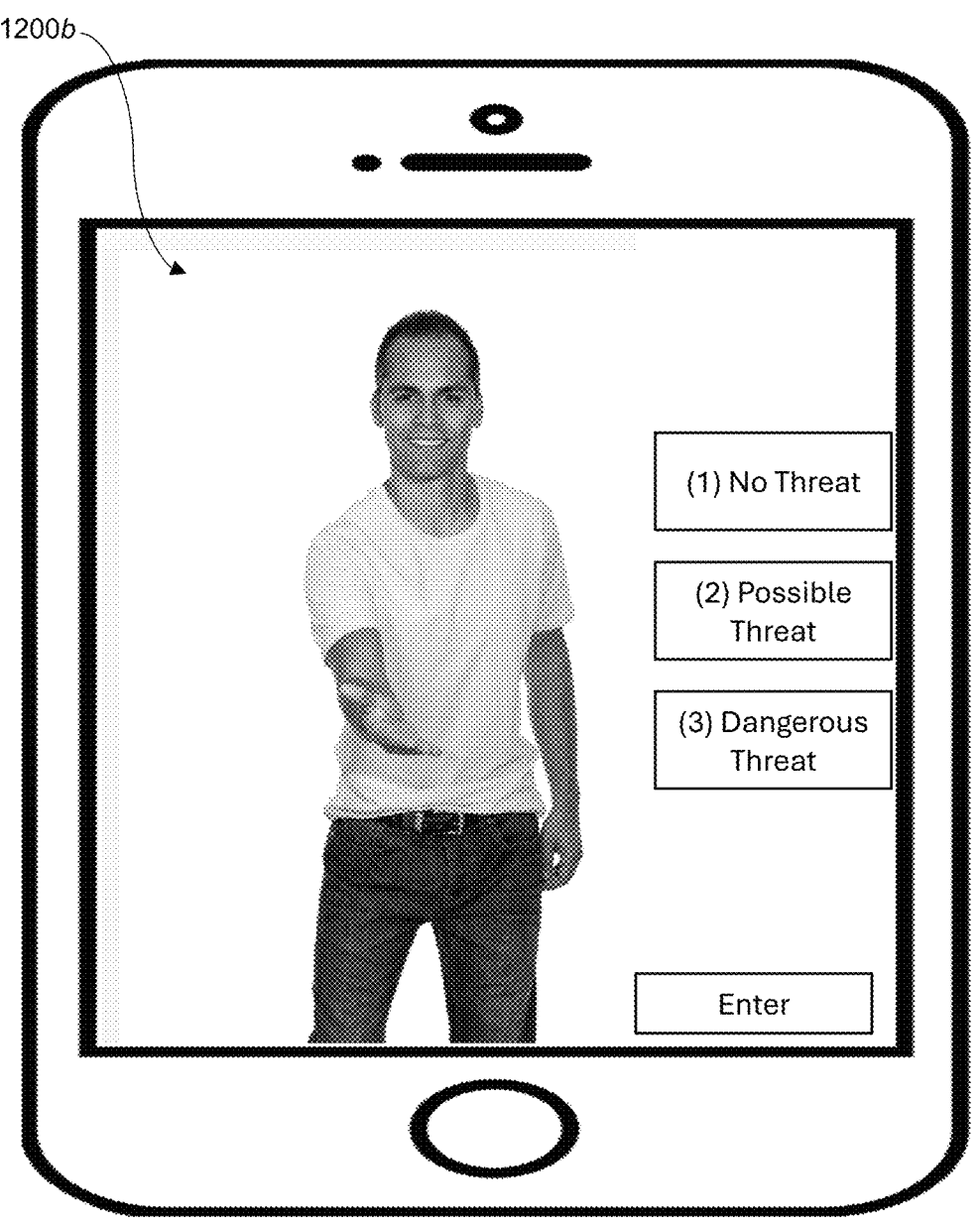
Figure 12C:
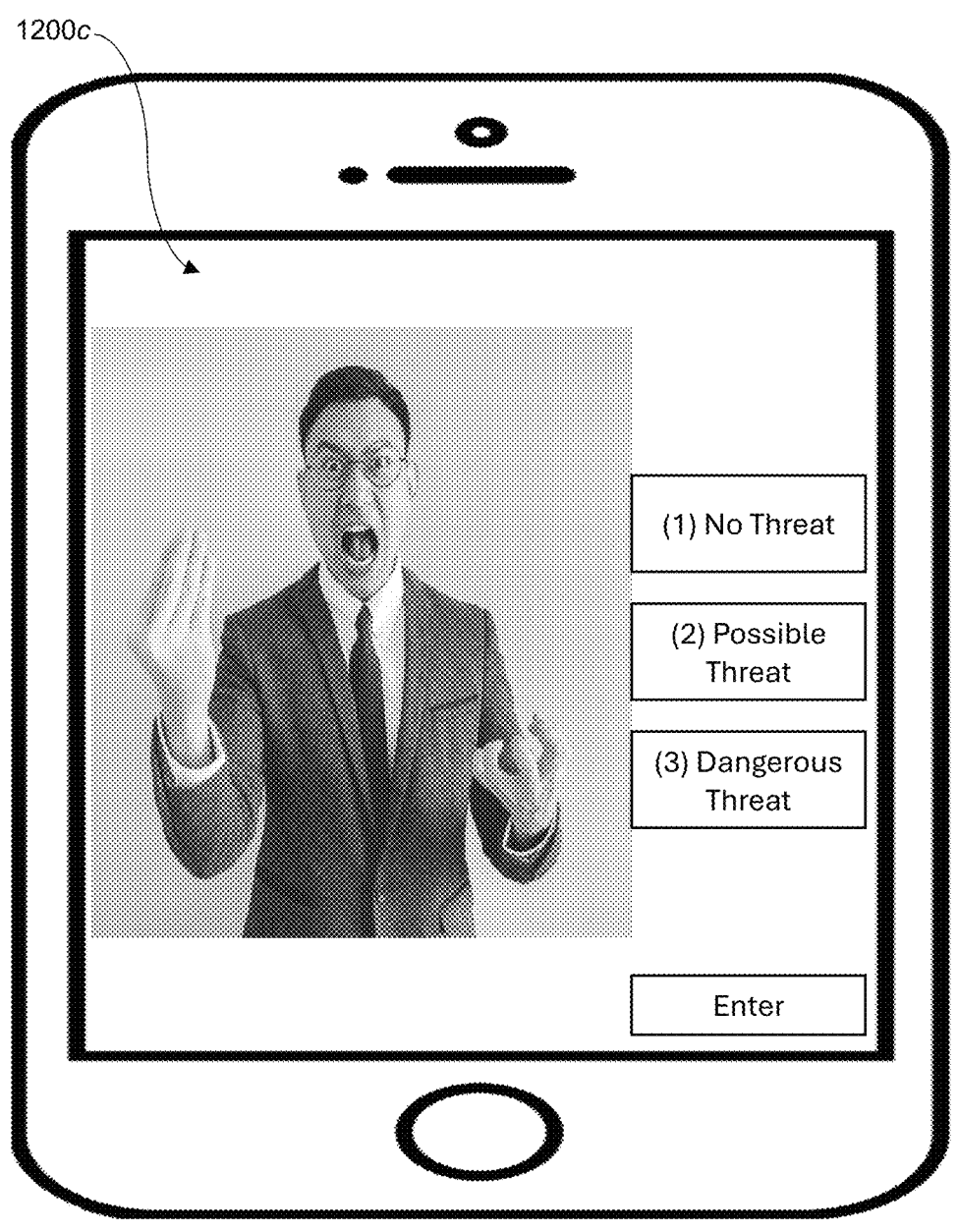

FIGS. 12B and 12C illustrate example threat assessment stimulus UI screens 1200b and 1200c, respectively, in which a visual stimulus (e.g., an image of a human subject) is displayed and the participant is prompted to classify the depicted stimulus using the permitted response classes. In the illustrated embodiment, the UI screens 1200b and 1200c include selectable response controls corresponding to "(1) No Threat," "(2) Possible Threat," and "(3) Dangerous Threat."

In various embodiments, upon selection of a response control (and optionally receipt of an additional confirmation input such as an "ENTER" input), the system records the participant response in association with a stimulus identifier for the displayed stimulus, and advances to a next stimulus according to a session policy. In certain embodiments, the system enforces a response window and/or presentation interval for each stimulus screen, such that responses are accepted only within an allowed time window, and missing/late responses may be recorded when no valid response is received within the window.

Figure 12D:
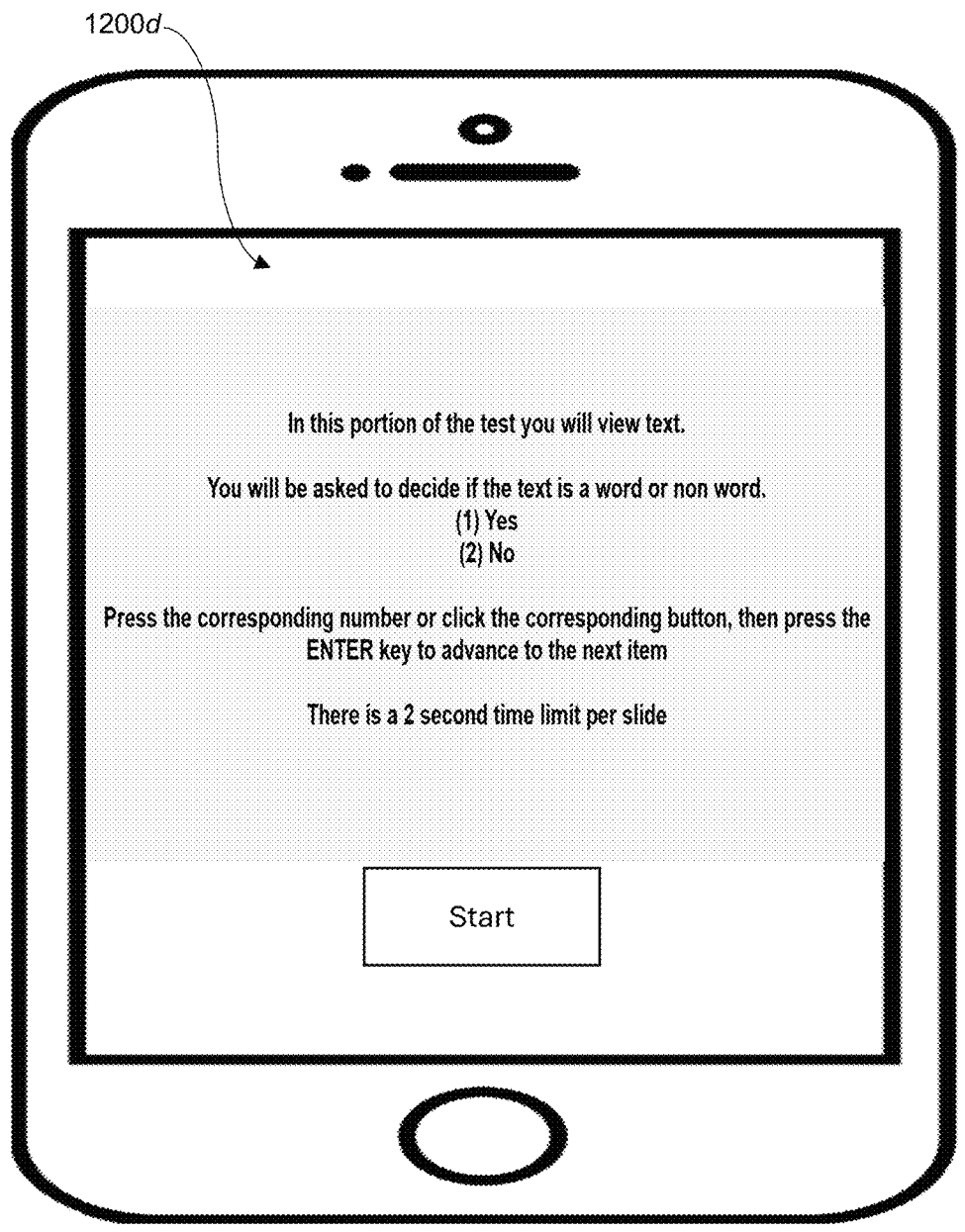

FIG. 12D illustrates an example instructional UI screen 1200d for a lexical decision portion of the test. In the illustrated embodiment, the instructional UI screen 1200d informs the participant that text (e.g., letter strings) will be presented and the participant will be asked to decide whether the presented text is a "word or non-word," with permitted responses including "(1) Yes" and "(2) No." The instructional UI screen 1200d further provides instructions to input a response by pressing a corresponding number or clicking a corresponding button and then pressing an "ENTER" key to advance, indicates a time limit per slide (e.g., 2 seconds), and includes a "Start" control for initiating the lexical decision portion.

Figure 12E:
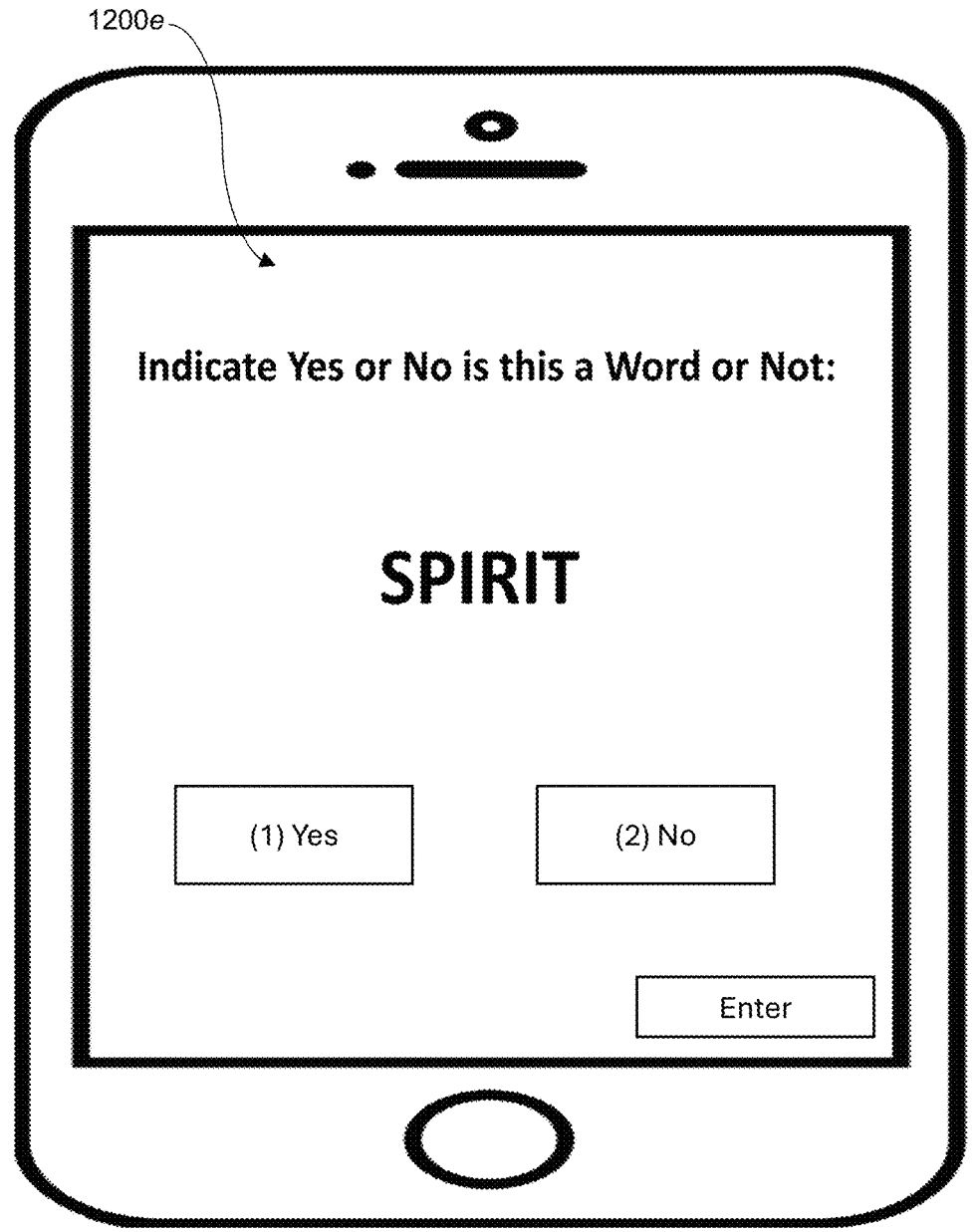
Figure 12F:
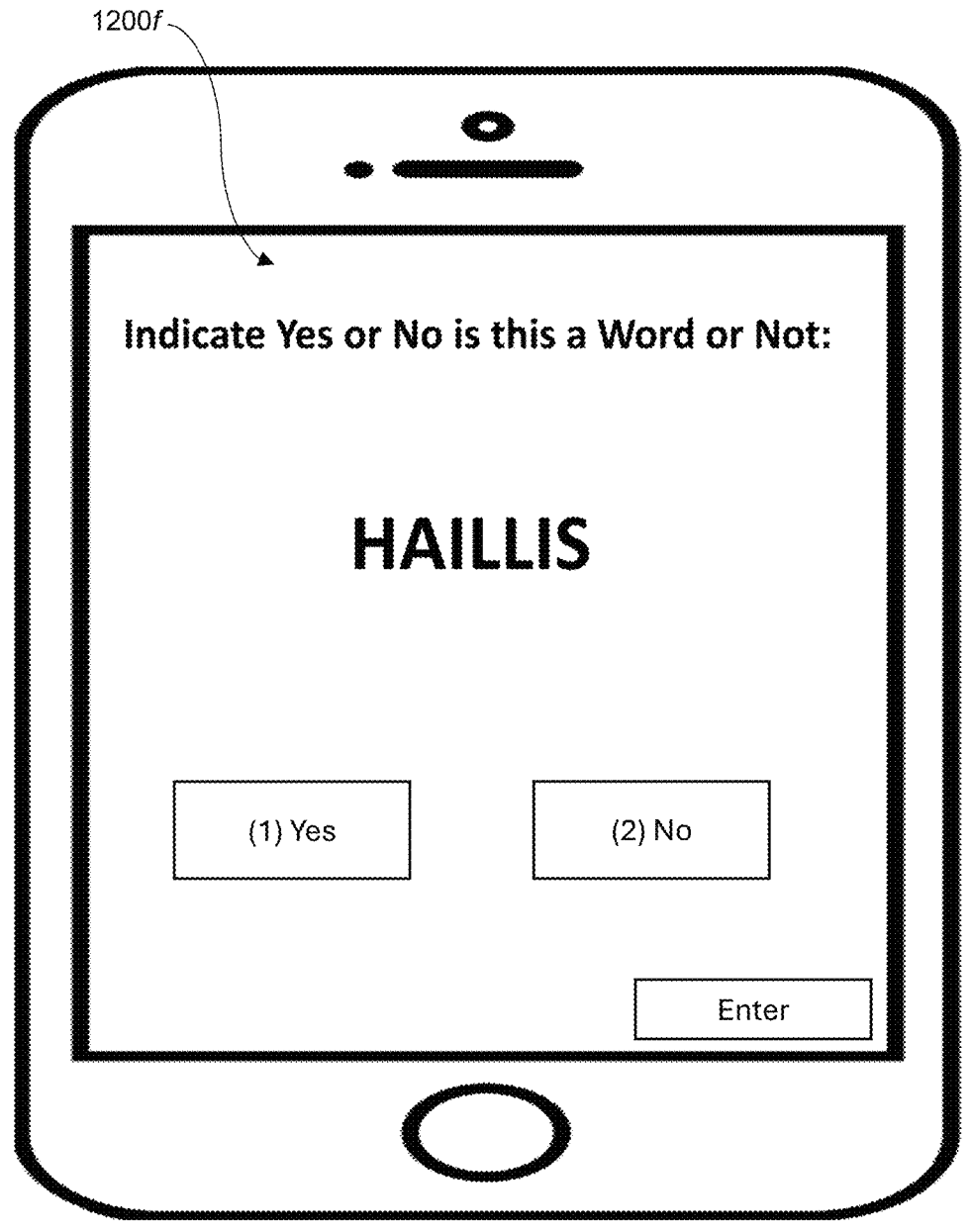

FIGS. 12E and 12F illustrate example lexical decision stimulus UI screens 1200e and 1200f, respectively. In the illustrated embodiment, each lexical decision stimulus UI screen presents a letter string (e.g., "SPIRIT" in FIG. 12E and "HAILLIS" in FIG. 12F) and provides response controls corresponding to "(1) Yes" and "(2) No" for indicating whether the presented letter string is a word. In various embodiments, the system captures the lexical decision response in association with an identifier for the presented letter string, determines correctness by comparison to a ground-truth label (word or non-word), and stores a per-stimulus lexical record including at least the response and timing information (e.g., response timestamp and/or response time). In certain embodiments, the system enforces a response window for each lexical stimulus screen such that late responses are rejected, ignored, or flagged as invalid, while still permitting recording of timing and/or validity indicators.

Figure 13:
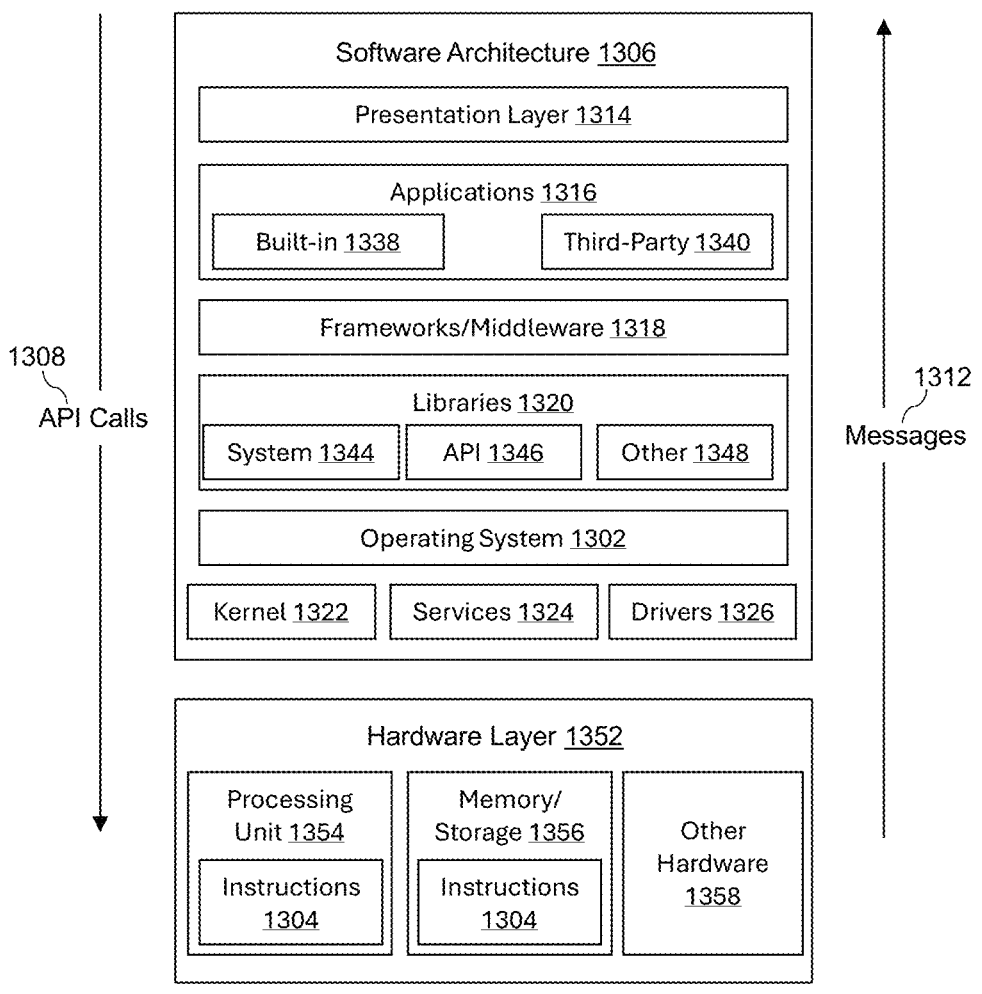
FIG. 13 is a block diagram illustrating a representative software architecture, which may be used in conjunction with various hardware architectures herein described.

FIG. 13 is a block diagram illustrating an exemplary software architecture 1306, which may be used in conjunction with various hardware architectures herein described. FIG. 13 is a non-limiting example of a software architecture, and it will be appreciated that many other architectures may be implemented to facilitate the functionality described herein. The software architecture 1306 may execute on hardware such as machine 1400 of FIG. 14 that includes, among other things, processors 1404, memory 1414, and I/O components 1418. A representative hardware layer 1352 is illustrated and can represent, for example, the machine 1400 of FIG. 14. The representative hardware layer 1352 includes a processing unit 1354 having associated executable instructions 1304. Executable instructions 1304 represent the executable instructions of the software architecture 1306, including implementation of the methods, components and so forth described herein. The hardware layer 1352 also includes memory or storage modules memory/storage 1356, which also have executable instructions 1304. The hardware layer 1352 may also comprise other hardware 1358.

As used herein, the term "component" may refer to a device, physical entity or logic having boundaries defined by function or subroutine calls, branch points, application program interfaces (APIs), or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions.

Components may constitute either software components (e.g., code embodied on a machine-readable medium) or hardware components. A "hardware component" is a tangible unit capable of performing certain operations and may be configured or arranged in a certain physical manner. In various exemplary embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations.

A hardware component may be a special-purpose processor, such as a Field-Programmable Gate Array (FPGA) or an Application Specific Integrated Circuit (ASIC). A hardware component may also include programmable logic or circuitry that is temporarily configured by software to perform certain operations. For example, a hardware component may include software executed by a processor or other programmable processor. Once configured by such software, hardware components become specific machines (or specific components of a machine) uniquely tailored to perform the configured functions and are no longer processors. It will be appreciated that the decision to implement a hardware component mechanically, in dedicated and permanently configured circuitry, or in temporarily configured circuitry (e.g., configured by software) may be driven by cost and time considerations.

A processor may be, or in include, any circuit, circuitry, or virtual circuit (a physical circuit emulated by logic executing on an actual processor) that manipulates data values according to control signals (e.g., "commands", "op codes", "machine code", etc.) and which produces corresponding output signals that are applied to operate a machine. A processor may, for example, be a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC) or any combination thereof. A processor may further be a multi-core processor having two or more independent processors (sometimes referred to as "cores") that may execute instructions contemporaneously. The processor as used herein may be a hardware component, which is in at least one of the devices, systems, servers and the like. The processor may include multiple cores and may be spread across multiple devices. The processor includes circuitry to execute instructions relating to the methods and structures described herein for determining relationships and outputting relationship data that is used by various device and their users.

Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a processor configured by software to become a special-purpose processor, the processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access.

For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components.

Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)). The performance of certain of the operations may be distributed among the processors, not only residing within a single machine, but deployed across a number of machines. In some exemplary embodiments, the processors or processor-implemented components may be located in a single geographic location (e.g., within a home environment, an office environment, or a server farm). In other exemplary embodiments, the processors or processor-implemented components may be distributed across a number of geographic locations.

In the exemplary architecture of FIG. 13, the software architecture 1306 may be conceptualized as a stack of layers where each layer provides particular functionality. For example, the software architecture 1306 may include layers such as an operating system 1302, libraries 1320, applications 1316 and a presentation layer 1314. Operationally, the applications 1316 or other components within the layers may invoke application programming interface (API) API calls 1308 through the software stack and receive messages 1312 in response to the API calls 1308. The layers illustrated are representative in nature and not all software architectures have all layers. For example, some mobile or special purpose operating systems may not provide a frameworks/middleware 1318, while others may provide such a layer. Other software architectures may include additional or different layers.

The operating system 1302 may manage hardware resources and provide common services. The operating system 1302 may include, for example, a kernel 1322, services 1324 and drivers 1326. The kernel 1322 may act as an abstraction layer between the hardware and the other software layers. For example, the kernel 1322 may be responsible for memory management, processor management (e.g., scheduling), component management, networking, security settings, and so on. The services 1324 may provide other common services for the other software layers. The drivers 1326 are responsible for controlling or interfacing with the underlying hardware. For instance, the drivers 1326 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 1320 provide a common infrastructure that is used by the applications 1316 or other components or layers. The libraries 1320 provide functionality that allows other software components to perform tasks in an easier fashion than to interface directly with the underlying operating system 1302 functionality (e.g., kernel 1322, services 1324 or drivers 1326). The libraries 1320 may include system libraries 1344 (e.g., C standard library) that may provide functions such as memory allocation functions, string manipulation functions, mathematical functions, and the like. In addition, the libraries 1320 may include API libraries 1346 such as media libraries (e.g., libraries to support presentation and manipulation of various media format such as MPREG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 1320 may also include a wide variety of other libraries 1348 to provide many other APIs to the applications 1316 and other software components/modules.

The frameworks/middleware 1318 (also sometimes referred to as middleware) provide a higher-level common infrastructure that may be used by the applications 1316 or other software components/modules. For example, the frameworks/middleware 1318 may provide various graphic user interface (GUI) functions, high-level resource management, high-level location services, and so forth. The frameworks/middleware 1318 may provide a broad spectrum of other APIs that may be utilized by the applications 1316 or other software components/modules, some of which may be specific to a particular operating system 1302 or platform. The applications 1316 include built-in applications 1338 or third-party applications 1340. The third-party applications 1340 may invoke the API calls 1308 provided by the operating system 1302 to facilitate functionality described herein.

The applications 1316 may use built in operating system functions (e.g., kernel 1322, services 1324 or drivers 1326), libraries 1320, and frameworks/middleware 1318 to create user interfaces to interact with users of the system. Alternatively, or additionally, in some systems interactions with a user may occur through a presentation layer, such as presentation layer 1314. In these systems, the application/component "logic" can be separated from the aspects of the application/component that interact with a user.

Figure 14:
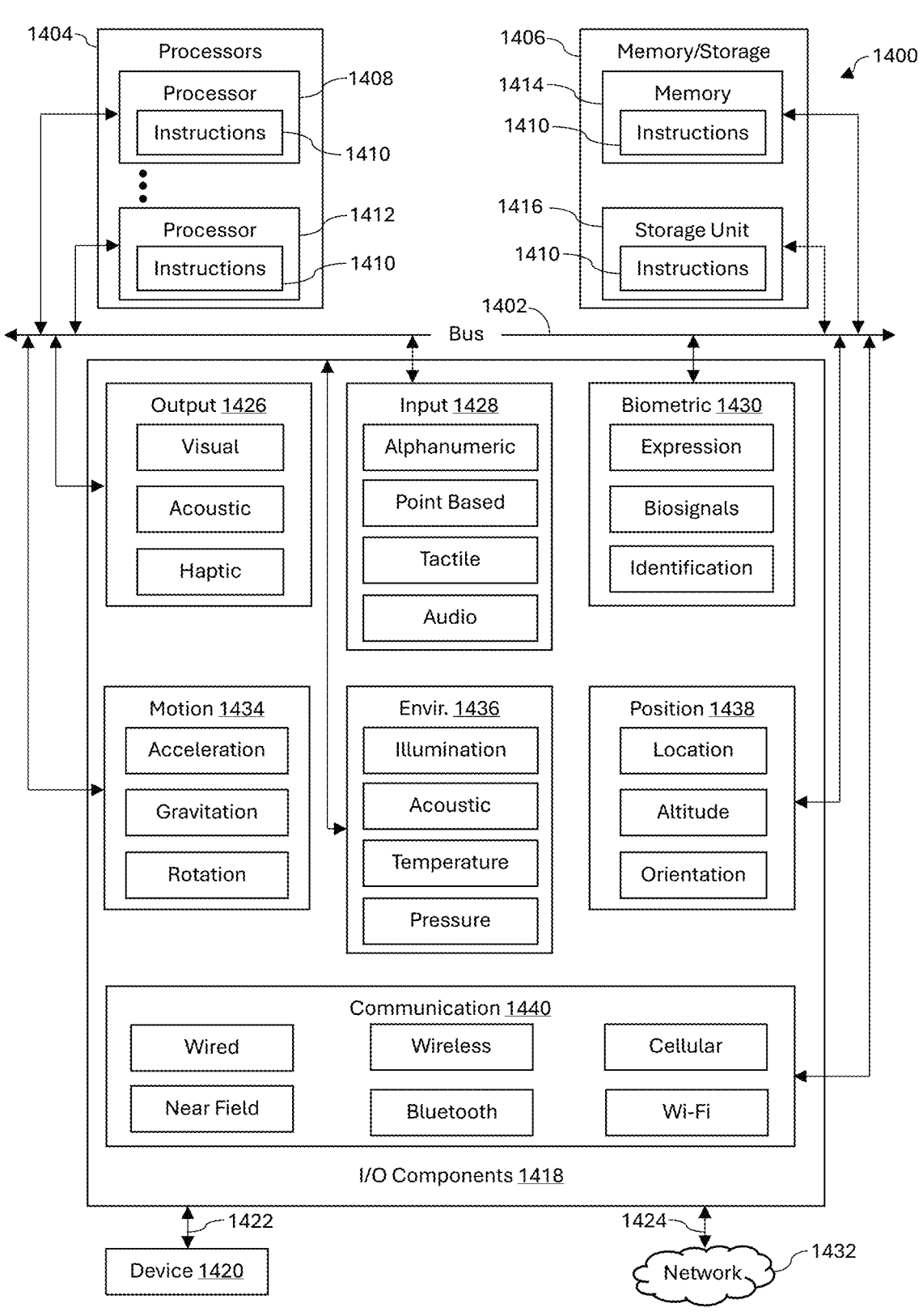
FIG. 14 is a block diagram illustrating components of a machine, according to some exemplary embodiments, able to read instructions from a machine-readable medium (e.g., a machine-readable storage medium) and perform any one or more of the methodologies discussed herein.

FIG. 14 is a block diagram illustrating components (also referred to herein as "modules") of a machine 1400, according to some exemplary embodiments, able to read instructions from a machine-readable medium (e.g., a machine-readable storage medium) and perform any one or more of the methodologies discussed herein. Specifically, FIG. 14 shows a diagrammatic representation of the machine 1400 in the example form of a computer system, within which instructions 1410 (e.g., software, a program, an application, an applet, an app, or other executable code) for causing the machine 1400 to perform any one or more of the methodologies discussed herein may be executed. As such, the instructions 1410 may be used to implement modules or components described herein. The instructions 1410 transform the non-programmed machine 1400 into a particular machine 1400 programmed to carry out the described and illustrated functions in the manner described. In alternative embodiments, the machine 1400 operates as a standalone device or may be coupled (e.g., networked) to other machines. In a networked deployment, the machine 1400 may operate in the capacity of a server machine or a client machine in a server-client network environment, or as a peer machine in a peer-to-peer (or distributed) network environment. The machine 1400 may comprise, but not be limited to, a server computer, a client computer, a personal computer (PC), a laptop computer, a network router, a network switch, a network bridge, or any machine capable of executing the instructions 1410, sequentially or otherwise, that specify actions to be taken by machine 1400. Further, while only a single machine 1400 is illustrated, the term "machine" shall also be taken to include a collection of machines that individually or jointly execute the instructions 1410 to perform any one or more of the methodologies discussed herein.

The machine 1400 may include processors 1404, memory memory/storage 1406, and I/O components 1418, which may be configured to communicate with each other such as via a bus 1402. The memory/storage 1406 may include a memory 1414, such as a main memory, or other memory storage, and a storage unit 1416, both accessible to the processors 1404 such as via the bus 1402. The storage unit 1416 and memory 1414 store the instructions 1410 embodying any one or more of the methodologies or functions described herein. The instructions 1410 may also reside, completely or partially, within the memory 1414, within the storage unit 1416, within at least one of the processors 1404 (e.g., within the processor's cache memory), or any suitable combination thereof, during execution thereof by the machine 1400. Accordingly, the memory 1414, the storage unit 1416, and the memory of processors 1404 are examples of machine-readable media.

As used herein, the term "machine-readable medium," "computer-readable medium," or the like may refer to any component, device or other tangible media able to store instructions and data temporarily or permanently. Examples of such media may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) or any suitable combination thereof. The term "machine-readable medium" should be taken to include a single medium or multiple media (e.g., a centralized or distributed database, or associated caches and servers) able to store instructions. The term "machine-readable medium" may also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" may refer to a single storage apparatus or device, as well as "cloud-based" storage systems or storage networks that include multiple storage apparatus or devices. The term "machine-readable medium" excludes signals per se.

The I/O components 1418 may include a wide variety of components to provide a user interface for receiving input, providing output, producing output, transmitting information, exchanging information, capturing measurements, and so on. The specific I/O components 1418 that are included in the user interface of a particular machine 1400 will depend on the type of machine. It will be appreciated that the I/O components 1418 may include many other components that are not shown in FIG. 14. The I/O components 1418 are grouped according to functionality merely for simplifying the following discussion and the grouping is in no way limiting. In various exemplary embodiments, the I/O components 1418 may include output components 1426 and input components 1428. The output components 1426 may include visual components (e.g., a display such as a plasma display panel (PDP), a light emitting diode (LED) display, a liquid crystal display (LCD), a projector, or a cathode ray tube (CRT)), acoustic components (e.g., speakers), other signal generators, and so forth. The input components 1428 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location or force of touches or touch gestures, or other tactile input components), audio input components (e.g., a microphone), and the like. The input components 1428 may also include one or more image-capturing devices, such as a digital camera for generating digital images or video.

In further exemplary embodiments, the I/O components 1418 may include biometric components 1430, motion components 1434, environmental environment components 1436, or position components 1438, as well as a wide array of other components. One or more of such components (or portions thereof) may collectively be referred to herein as a "sensor component" or "sensor" for collecting various data related to the machine 1400, the environment of the machine 1400, a user of the machine 1400, or a combinations thereof.

Communication may be implemented using a wide variety of technologies. The I/O components 1418 may include communication components 1440 operable to couple the machine 1400 to a network 1432 or devices 1420 via coupling 1422 and coupling 1424 respectively. For example, the communication components 1440 may include a network interface component or other suitable device to interface with the network 1432. In further examples, communication components 1440 may include wired communication components, wireless communication components, cellular communication components, Near Field Communication (NFC) components, Bluetooth® components (e.g., Bluetooth® Low Energy), Wi-Fi components, and other communication components to provide communication via other modalities. The devices 1420 may be another machine or any of a wide variety of peripheral devices (e.g., a peripheral device coupled via a Universal Serial Bus (USB)). Moreover, the communication components 1440 may detect identifiers or include components operable to detect identifiers.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general-purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

Any publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

Where a phrase similar to "at least one of A, B, or C," "at least one of A, B, and C," "one or more A, B, or C," or "one or more of A, B, and C" is used, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

Embodiments of the present invention are described above with reference to flowcharts and/or block diagrams. It will be understood that phases of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While certain exemplary embodiments have been described and shown in the accompanying drawings, it is to be understood that such embodiments are merely illustrative of, and not restrictive on, the broad invention, and that this invention is not limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A computerized behavioral measurement system comprising:
    a display;
    one or more input devices;

at least one processor; and a memory storing instructions that, when executed by the at least one processor, cause the system to:

present, via the display, a sequence of visual stimuli, wherein each visual stimulus in the sequence of visual stimuli is associated with a stimulus identifier and a stimulus category, wherein the sequence of visual stimuli include a sequence of photographs of human subjects, wherein the stimulus identifier comprises race or ethnicity of the human subjects, wherein the stimulus category comprises a level of threat associated with the human subjects;

enforce, for each visual stimulus in the sequence of visual stimuli, at least one of (i) a presentation interval and (ii) a response window;

receive, via the one or more input devices and during the response window, one or more participant response, wherein the one or more participant response is associated with the stimulus identifier;

measure, during presentation of each visual stimulus in the sequence of visual stimuli, an interaction metric comprising a dwell-time metric associated with at least one of (a) each visual stimulus in the sequence of visual stimuli or (b) a region-of-interest of each visual stimulus in the sequence of visual stimuli;

generate, from the one or more participant response and the interaction metric, a machine-readable output record comprising one or more category-segmented response metric for a participant;

normalize the one or more category-segmented response metric to generate an ipsative metric for the participant, wherein generating the ipsative metric for the participant comprises computing a deviation of the one or more category-segmented response metric from an aggregate metric across the stimulus categories for the visual stimuli for the participant; and store the machine-readable output record in a non-transitory storage medium.

2. The computerized behavioral measurement system of claim 1, wherein measuring the dwell-time metric comprises measuring, without expressly prompting the participant to provide the dwell-time metric, an elapsed time corresponding to participant attention to each visual stimulus in the sequence of visual stimuli based on event data captured by the system.

3. The computerized behavioral measurement system of claim 2, wherein the event data comprises at least one of cursor-position events, pointer-movement events, click events, keystroke events, scrolling events, viewport-focus events, window-focus events, or touch-input events.

4. The computerized behavioral measurement system of claim 1, wherein the region-of-interest is defined by region metadata stored in association with the stimulus identifier.

5. The computerized behavioral measurement system of claim 1, wherein enforcing the presentation interval and/or the response window comprises disabling at least one of (i) stimulus skipping, (ii) stimulus replay, (iii) stimulus backtracking, or (iv) response submission outside the response window.

6. The computerized behavioral measurement system of claim 1, wherein presenting the sequence of visual stimuli comprises selecting the sequence according to a session policy that enforces a minimum quantity of stimuli per stimulus category.

7. The computerized behavioral measurement system of claim 1, wherein the one or more category-segmented response metric comprises at least one of per-category accuracy, per-category error rate, per-category response-distribution statistics, per-category dwell-time statistics, or per-category response-time statistics.

8. The computerized behavioral measurement system of claim 1, wherein measuring the dwell-time metric comprises accumulating elapsed time while event data indicates a participant focus within the region-of-interest.

9. A computer-implemented method comprising:

presenting, on a display, a sequence of visual stimuli, wherein each visual stimulus in the sequence of visual stimuli is associated with a stimulus identifier and a stimulus category, wherein the sequence of visual stimuli includes a sequence of photographs of human subjects, wherein the stimulus identifier comprises race or ethnicity of the human subjects, wherein the stimulus category comprises a level of threat associated with the human subjects;

for each visual stimulus in the sequence of visual stimuli, enforcing a presentation interval and a response window;

capturing one or more participant response associated with the stimulus identifier during the response window;

measuring, during the presentation of each visual stimulus in the sequence of visual stimuli, an interaction metric comprising a dwell-time metric associated with at least one of each visual stimulus in the sequence of visual stimuli or a region-of-interest of each visual stimulus in the sequence of visual stimuli;

generating, based on the one or more participant response and the interaction metric, one or more category-segmented response metric for a participant;

normalizing the one or more category-segmented response metric to generate an ipsative metric for the participant, wherein generating the ipsative metric for the participant comprises computing a deviation of the one or more category-segmented response metric from an aggregate metric across the stimulus categories for the visual stimuli for the participant; and outputting and storing a machine-readable output record comprising the one or more category-segmented response metric.

10. The computer-implemented method of claim 9, wherein normalizing comprises scaling at least one category-segmented response metric in the one or more category-segmented response metric for the participant using at least one of z-score normalization, min-max scaling, rank-order normalization, or vector normalization.

11. The computer-implemented method of claim 9, wherein measuring the dwell-time metric comprises computing the dwell-time metric from event data without expressly requesting the dwell-time metric from the participant.

12. The computer-implemented method of claim 9, wherein generating the one or more category-segmented response metric comprises generating at least one of an under-classification rate, an over-classification rate, or a confusion matrix based on the one or more participant response mapped to a set of allowed response classes.

13. The computer-implemented method of claim 9, wherein the enforcing comprises disabling at least one of stimulus backtracking, stimulus replay, or response entry outside the response window.

14. The computer-implemented method of claim 9, further comprising storing, in association with the machine-readable output record, session metadata comprising at least one of device identifiers, display parameters, timing parameters, or an ordering of the presented stimuli.

15. A computerized behavioral testing system comprising:

a display;

one or more input devices;

at least one processor; and a memory storing instructions that, when executed by the at least one processor, cause the system to:

execute a first task module that presents scenario-based visual stimuli and captures participant classification responses under enforced response windows, wherein the scenario-based visual stimuli comprise photographs of human subjects including predetermined characteristics comprising (1) race or ethnicity and (2) facial expression;

execute a second task module that presents lexical stimuli comprising letter strings and captures participant lexical-decision responses indicating whether each letter string is a word or a non-word under the enforced response windows;

compute, for the first task module, at least one category-segmented visual-task metric;

compute, for the second task module, at least one lexical-task metric comprising a lexical error rate; and generate and store a unified machine-readable output record comprising the at least one category-segmented visual-task metric and the at least one lexical-task metric for a participant.

16. The computerized behavioral testing system of claim 15, wherein the first task module further measures an interaction metric comprising a dwell-time metric associated with at least one visual stimulus of the scenario-based visual stimuli or a region-of-interest of the at least one visual stimulus of the scenario-based visual stimuli.

17. The computerized behavioral testing system of claim 15, wherein the lexical stimuli comprise at least two lexical stimulus sets selected from a static word set, an emotive word set, and a nonsense letter-string set.

18. The computerized behavioral testing system of claim 15, wherein the system further comprises a session orchestrator configured to interleave the first task module and the second task module according to a session policy that enforces at least one of randomized ordering, counterbalanced ordering, or minimum counts per task module.

19. The computerized behavioral testing system of claim 15, wherein generating the unified machine-readable output record comprises generating a participant-specific output vector comprising at least (i) the at least one category-segmented visual-task metric, (ii) the lexical error rate, and (iii) at least one timing-derived metric.

20. The computerized behavioral testing system of claim 15, wherein the system is configured to export the unified machine-readable output record in a structured format comprising at least one of JSON, XML, or a tabular file format for downstream processing by an external computing system.

* * * * *